(12) United States Patent
Bikson

(10) Patent No.: US 11,878,284 B2
(45) Date of Patent: Jan. 23, 2024

(54) MESOPOROUS POLY (ARYL ETHER KETONE) HOLLOW FIBER MEMBRANES AND USE THEREOF IN MASS TRANSFER PROCESSES

(71) Applicant: Avanpore LLC, Newton, MA (US)

(72) Inventor: Benjamin Bikson, Newton, MA (US)

(73) Assignee: Avanpore LLC, Newton, MA (US)

( * ) Notice: Subject to any disclaimer, the term of this patent is extended or adjusted under 35 U.S.C. 154(b) by 0 days.

(21) Appl. No.: 18/124,130

(22) Filed: Mar. 21, 2023

(65) Prior Publication Data
US 2023/0219062 A1 Jul. 13, 2023

Related U.S. Application Data

(60) Division of application No. 17/957,551, filed on Sep. 30, 2022, now abandoned, which is a continuation of (Continued)

(51) Int. Cl.
 *C08J 9/26* (2006.01)
 *B01J 19/24* (2006.01)
 (Continued)

(52) U.S. Cl.
 CPC ...... *B01J 20/28038* (2013.01); *B01D 61/246* (2013.01); *B01D 63/02* (2013.01);
 (Continued)

(58) Field of Classification Search
 CPC .............. B01J 20/28038; B01J 20/262; B01J 20/28011; B01J 20/28083; B01J 20/28085;
 (Continued)

(56) References Cited

U.S. PATENT DOCUMENTS 3,735,558 A 5/1973 Skarstrom et al.
3,755,034 A 8/1973 Mahon et al.
(Continued)

OTHER PUBLICATIONS

Andrea Adamo, Patrick L. Heider, Nopphon Weeranoppanant, and Klavs F. Jensen, "Membrane-Based, Liquid-Liquid Separator with Integrated Pressure Control", Industrial and Engineering Chemistry Research, (2013), V. 52, pp. 10802-10808.
(Continued)

*Primary Examiner* — Dirk R Bass
(74) *Attorney, Agent, or Firm* — FORGE IP, PLLC

(57) ABSTRACT

A process for the efficient transfer of molecules between phases employing mesoporous poly (aryl ether ketone) hollow fiber membranes is provided. The method addresses the controlled transfer of reactants into and removal of reaction products from a reaction media and the removal and separation of target molecules from process streams by membrane-assisted liquid-liquid extraction. A number of possible modes of liquid-liquid extraction are possible according to the invention by utilizing porous poly (aryl ether ketone) hollow fiber membranes of Janus-like structure that exhibit a combination of hydrophilic and hydrophobic surface characteristics. The method of the present invention can address the continuous manufacture of chemicals in membrane reactors and is useful for a broad range of separation applications, including separation and recovery of active pharmaceutical ingredients.

26 Claims, 4 Drawing Sheets

Related U.S. Application Data application No. 17/836,575, filed on Jun. 9, 2022, now Pat. No. 11,491,464.

(60) Provisional application No. 63/214,504, filed on Jun. 24, 2021.

(51) Int. Cl.

| | |
|---|---|
| *B01J 10/00* | (2006.01) |
| *B01J 20/28* | (2006.01) |
| *B01J 20/26* | (2006.01) |
| *B01J 20/30* | (2006.01) |
| *B01J 20/32* | (2006.01) |
| *C07C 7/12* | (2006.01) |
| *C07C 7/11* | (2006.01) |
| *B01D 69/08* | (2006.01) |
| *B01D 71/52* | (2006.01) |
| *B01D 69/02* | (2006.01) |
| *B01D 61/24* | (2006.01) |
| *B01D 67/00* | (2006.01) |
| *B01D 63/02* | (2006.01) |

(52) U.S. Cl.
CPC ......... *B01D 67/0023* (2013.01); *B01D 69/02* (2013.01); *B01D 69/08* (2013.01); *B01D 71/52* (2013.01); *B01J 10/00* (2013.01); *B01J 19/2475* (2013.01); *B01J 20/262* (2013.01); *B01J 20/28011* (2013.01); *B01J 20/28035* (2013.01); *B01J 20/28083* (2013.01); *B01J 20/28085* (2013.01); *B01J 20/3064* (2013.01); *B01J 20/3217* (2013.01); *C07C 7/11* (2013.01); *C07C 7/12* (2013.01); *C08J 9/26* (2013.01); *B01D 2325/022* (2013.01); *B01D 2325/36* (2013.01); *B01D 2325/38* (2013.01); *C08J 2201/0462* (2013.01); *C08J 2205/042* (2013.01); *C08J 2371/10* (2013.01)

(58) Field of Classification Search
CPC . B01J 20/3064; B01J 20/3217; B01D 61/246; B01D 63/02; B01D 67/0023; B01D 69/02; B01D 69/08; B01D 71/52; B01D 2325/022; B01D 2325/36; B01D 2325/38; C07C 7/11; C07C 7/12
See application file for complete search history.

(56) References Cited

U.S. PATENT DOCUMENTS

| | | |
|---|---|---|
| 3,794,468 A | 2/1974 | Leonard |
| 3,956,112 A | 5/1976 | Lee et al. |
| 4,207,192 A | 6/1980 | Coplan et al. |
| 4,721,732 A | 1/1988 | Dubrow et al. |
| 4,881,955 A | 11/1989 | Bikson et al. |
| 4,957,817 A | 9/1990 | Chau et al. |
| 4,966,707 A | 10/1990 | Cussler et al. |
| 4,992,485 A | 2/1991 | Koo et al. |
| 4,997,569 A | 3/1991 | Sirkar |
| 5,026,479 A | 6/1991 | Bikson et al. |
| 5,064,580 A | 11/1991 | Beck et al. |
| 5,089,192 A | 2/1992 | Costa |
| 5,205,968 A | 4/1993 | Damrow et al. |
| 5,224,522 A | 7/1993 | Baurmeister |
| 5,227,101 A | 7/1993 | Mahoney et al. |
| 5,260,415 A | 11/1993 | David |
| 5,263,982 A | 11/1993 | Shimomura et al. |
| 5,282,964 A | 2/1994 | Young et al. |
| 5,507,949 A | 4/1996 | Ho |
| 5,598,874 A | 2/1997 | Alei et al. |
| 5,651,931 A | 7/1997 | Bailey et al. |
| 5,702,601 A | 12/1997 | Bikson et al. |
| 5,714,072 A | 2/1998 | Reed et al. |
| 5,837,033 A | 11/1998 | Giglia et al. |
| 5,997,741 A | 12/1999 | Shimoda et al. |
| 6,017,455 A | 1/2000 | Shimoda et al. |
| 6,433,163 B1 | 8/2002 | Ho |
| 6,887,408 B2 | 5/2005 | Yuan |
| 7,176,273 B2 | 2/2007 | Yuan et al. |
| 7,229,580 B2 | 6/2007 | Yuan |
| 7,264,725 B2 | 9/2007 | Vido et al. |
| 7,368,526 B2 | 5/2008 | Yuan et al. |
| 7,407,609 B2 | 8/2008 | Brown |
| 7,439,291 B2 | 10/2008 | Wang et al. |
| 8,690,994 B2 | 4/2014 | Taylor et al. |
| 9,610,547 B2 | 4/2017 | Ding et al. |
| 9,782,726 B2 | 10/2017 | Seibert et al. |
| 9,833,737 B2 | 12/2017 | Ahn et al. |
| 9,908,985 B2 | 3/2018 | Iliuta et al. |
| 9,962,629 B2 | 5/2018 | Taylor et al. |
| 10,035,881 B2 | 7/2018 | Ahn et al. |
| 10,076,620 B2 | 9/2018 | Schmidt et al. |
| 10,328,425 B2 | 6/2019 | Haring |
| 10,376,846 B2 | 8/2019 | Ding et al. |
| 10,392,271 B2 | 8/2019 | Janson et al. |
| 10,456,738 B2 | 10/2019 | Ahn et al. |
| 2006/0094852 A1 | 5/2006 | Yuan et al. |

OTHER PUBLICATIONS

Gong Chen, Yuan Chen, Tingjian Huang, Zhongchen He, Jianjun Xu and Pengqing Liu, "Pore Structure and Properties of PEEK Hollow Fiber Membranes: Influence of the Phase Structure Evolution of PEEK/PEI Composite", Polymers, (2019), V. 11 p. 1398.

Yong Ding and Ben Bikson, "Preparation and characterization of semi-crystalline poly(ether ether ketone) hollow fiber membranes", Journal of Membrane Science, (2010), V. 357 pp. 192-198.

A. Dupuy, V. Athes, J. Schenk, U. Jenelten, and I. Souchon, "Experimental and theoretical considerations on breakthrough pressure in membrane-based solvent extraction: Focus on citrus essential oil/hydro-alcoholic solvent systems with low interfacial tension", Journal of Membrane Science, (2011), V. 378, pp. 203-213.

Bernhard Gutmann, David Cantillo, and C. Oliver Kappe, Continuous-flow technology—A Tool for the Safe Manufacturing of Active Pharmaceutical Ingredients, Angewandte Review, Angew. Chem. Int. Ed., (2015), V. 54, pp. 6688-6728.

T. He et al., "Composite hollow fiber membranes for organic solvent-based liquid-liquid extraction", Journal of Membrane Science, V.234, (2004), pp. 1-10.

Catherine Henneuse, Bernard Goret and Jacqueline Marchand-Brynaert, "Surface carboxylation of PEEK film by selective wet-chemistry", Polymer, (1998), V. 39, No. 4, pp. 835-844.

Catherine Henneuse-Boxus, Eric Duliere, Jacqueline Marchand-Brynaert, "Surface functionalization of PEEK film using photo-chemical routes", European Polymer Journal, (2001), V. 37 pp. 9-18.

C. Henneuse-Boxusa, A. De Rob, P. Bertrand, J. Marchand-Brynaert, "Covalent attachment of fluorescence probes on the PEEK-OH film surface", Polymer, (2000), V. 41 pp. 2339-2348.

Tao Huang, Jianfeng Song, Sanfeng He, Tao Li, Xue-Mei Li, and Tao He, "Enabling sustainable green close-loop membrane lithium extraction by acid and solvent resistant poly (ether ether ketone) membrane", Journal of Membrane Science, (2019), V. 589, pp. 117273.

Janke Jönsson, Lennart Mathiasson, "Membrane extraction in analytical chemistry", J. Sep. Sci., (2001), V. 24, p. 495.

A. Kiani, R.R. Bhave and K.K. Sirkar "Solvent extraction with immobilized interfaces in microporous hydrophobic membranes", Journal of Membrane Science, (1984), V. 20, pp. 125-145.

Z. Lazarova, B. Syska and K. Schugerl, "Application of large-scale hollow fiber membrane contactors for simultaneous extraction removal and stripping of penicillin G", Journal of Membrane Science, V. 202, (2002), p. 151.

Jorge L. Lopez, Stephen L. Matson, A multiphase/extractive enzyme membrane reactor for production of diltiazem chiral intermediate:, Journal of Membrane Science, (1997), V. 125, pp. 189-211.

(56) References Cited

OTHER PUBLICATIONS

Rakesh H. Mehta, David A. Madsen, Douglass S. Kalika, "Microporous membranes based on poly(ether ether ketone) via thermally-induced phase separation", Journal of Membrane Science, (1995), V. 107, pp. 93-106.

Olivier Noiset, Catherine Henneuse, Yves-Jacques Schneider, and Jacqueline Marchand-Brynaert, "Surface Reduction of Poly (aryl ether ether ketone) Film: UV Spectrophotometric, 3H Radiochemical, and X-ray Photoelectron Spectroscopic Assays of the Hydroxyl Functions", Macromolecules, (1997), V. 30, pp. 540-548.

Olivier Noiset, et al. "Surface Modification of Poly(aryl ether ether ketone) (PEEK) Film by Covalent Coupling of Amines and Amino Acids through a Spacer Arm", Journal of Polymer Science: Part A: Polymer Chemistry, (1997), vol. 35, pp. 3779-3790.

Stig Pedersen-Bjergaard, and Knut Einar Rasmussen, "Liquid-phase microextraction with porous hollow fibers, a miniaturized and highly flexible format for liquid-liquid extraction", Journal of Chromatography A, (2008), V. 1184, pp. 132-142.

Ravi Prasad et al., "Further studies on solvent extraction with immobilized interfaces in a microporous hydrophobic membrane", Journal of Membrane Science, (1986), V. 26, pp. 79-97.

Ravi Prasad and K. K. Sirkar, "Solvent Extraction with Microporous Hydrophilic and Composite Membranes", AIChE Journal, (1987), vol. 33, p. 1057.

R. Prasad et al. "Novel Liquid-In-Pore Configurations in Membrane Solvent Extraction", AIChE Journal, (1990), vol. 36, p. 1592.

Lydia N. Rodrigues, Kamalesh K. Sirkar, Kirk Ryan Weisbrod, John C. Ahern, and Uwe Beuscher, "Porous hydrophobic-hydrophilic Janus membranes for nondispersive membrane solvent extraction", Journal of Membrane Science, (2021), V. 637, 119633.

Miroslav Stanojevic et al. "Review of membrane contactors designs and application of different modules in industry", FME Transactions (2003), V. 31, pp. 91-98.

A. M. Vaidya et al., "Aqueous-Organic Bioreactor. Part 1 A Guide to Membrane Selection", Journal of Membrane Science, (1992), vol. 71, p. 139.

Zhecun Wang, Xiaoqiu Liu, Jing Guo, Tauqir A. Sherazi, Suobo Zhang, and Shenghai Li, "A liquid-based Janus porous membrane for convenient liquid-liquid extraction and immiscible oil/water separation", Chem. Communications., (2019), V. 55, p. 14486.

Hao-Cheng Yang, Jingwei Hou, Vicki Chen, and Zhi-Kang Xu, "Janus Membranes: Exploring Duality for Advanced Separation", Angew. Chem. Int. Ed. (2016), V. 55, pp. 2-12.

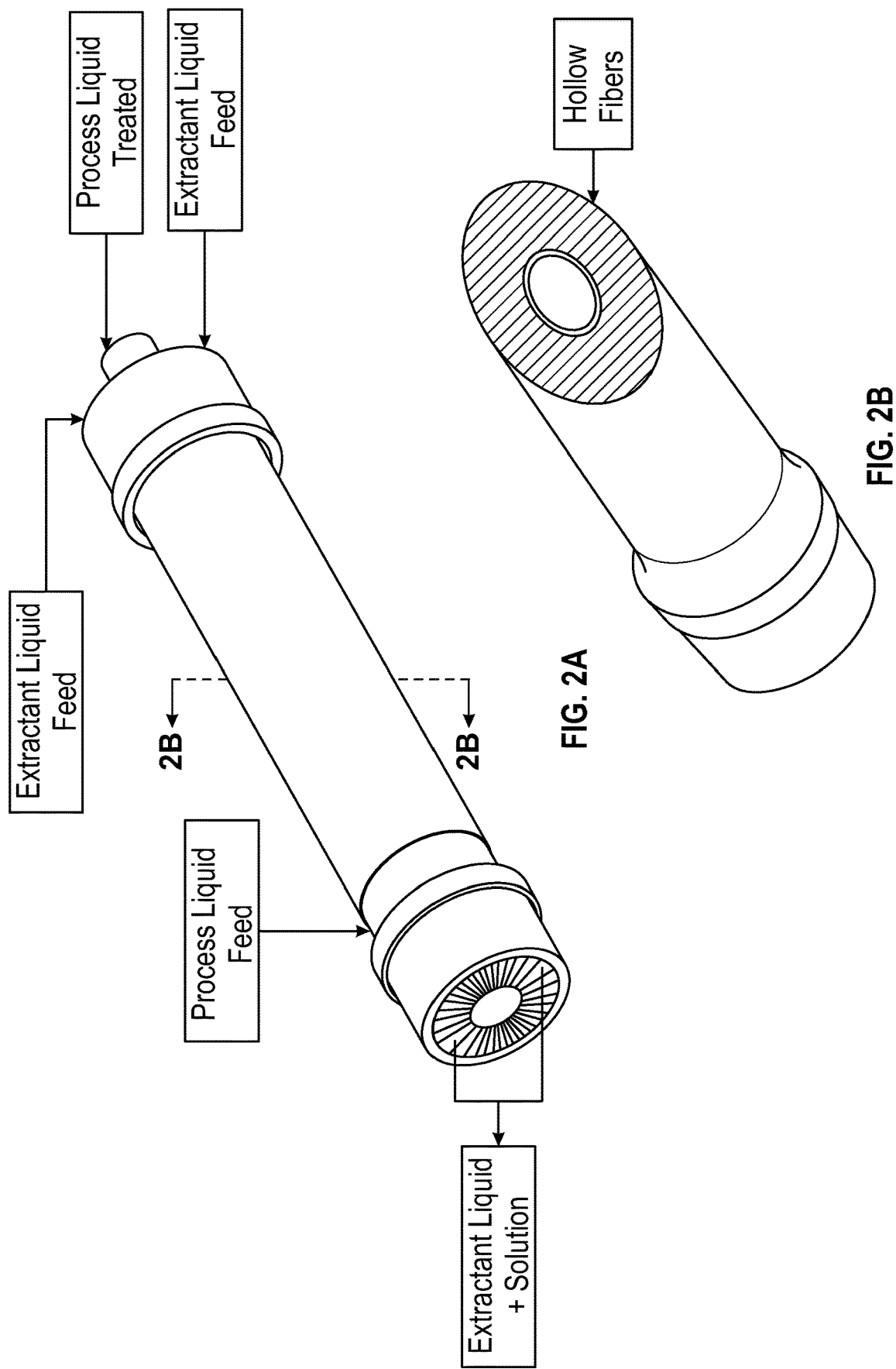

MESOPOROUS POLY (ARYL ETHER KETONE) HOLLOW FIBER MEMBRANES AND USE THEREOF IN MASS TRANSFER PROCESSES

FIELD OF THE INVENTION

This invention relates to the preparation and use of porous polymeric hollow fiber membranes for a broad range of mass transfer processes, including the transfer of molecules into fluid reactive media, removing reaction products from fluid reaction media, and liquid-liquid extraction applications.

BACKGROUND OF THE INVENTION

Porous polymeric membranes are well known in the art and are used widely for filtration and purification processes, such as filtration of wastewater, desalination, preparation of ultra-pure water, and in medical, pharmaceutical, or food applications, including removal of microorganisms, dialysis, and protein filtration. A membrane is generally defined as a partition that permits the passage of one or more components through the membrane between two phases. The transfer of molecules can be selective, wherein the membrane retains one or more components while allowing passage of other components, or can serve as a non-selective partition between the phases enabling efficient molecular transfer; in the latter case the membrane serves as a contactor. Porous polymeric membranes are used to separate components of liquid mixtures by membrane distillation and as contactors to facilitate dissolution of gases in liquids or to remove gases from liquids, as membrane reactors, and in numerous other applications where they serve as a generic phase separator, for example, as a battery separator. The application spectrum of membrane processes stretches from filtration of solids up to separations on a molecular level. Pressure-driven membrane processes, such as microfiltration (MF), ultrafiltration (UF), nanofiltration (NF) and reverse osmosis (RO), are established large-scale industrial processes for water purification and recovery of high-value substances. Initially applied to water-based systems, membrane separations are increasingly applied to non-water solvent-based systems as well.

Many industrially important chemical transformations involve molecular transfer between multiple phases (gas-liquid, solid-liquid, liquid-liquid, or solid-liquid-gas). In multi-phase chemical processes, efficient transfer of molecules between the phases is necessary for an efficient generation of reaction products with reduced byproduct formation. Conventional batch or semi-batch reactor-based processes can suffer from low mass and heat transfer due to small surface-to-volume ratios. Interface mixing in large commercial scale batch reactors continues to present challenges and can suffer from the formation of localized hot spots in exothermic reactions leading to safety concerns. The rate of mass transfer is important in biphasic systems where the overall reaction rate is affected by the rate of transfer of active species between the two phases. Continuous flow membrane reactors have the potential to mitigate challenges (including safety challenges) associated with using batch reactors by enabling the controlled introduction of reactants into the reaction media and controlled removal of products or byproducts from the reaction media. Furthermore, the membrane-assisted molecular transfer between the phases can take place with or without phase intermixing and selectively or non-selectively. The molecular transfer between the phases can be carried out to affect and control a chemical reaction (i.e., utilizing a membrane device as a chemical reactor), to separate individual components from a reaction mixture (i.e., utilizing a membrane device as a stand-alone separator), or as a combined membrane/reaction product separator in a single device.

Frequently, the transfer of molecules between the phases must be accomplished without an excessive phase intermixing that can lead to difficulties in downstream processing. A porous membrane positioned between the phases can enable the transfer of molecules without phase intermixing. Membrane reactor design is important for achieving efficient mass transfer while suppressing phase intermixing. Generally, hollow fiber membrane systems provide for an increased surface area to volume ratio in reactor devices as compared to flat sheet membrane configurations. In multiphasic systems, the interfacial area plays an important role in phase transfer, which can be rate-limiting. For this reason, hollow fiber membrane systems tend to outperform their flat sheet counterparts. For each of these multiphasic systems, different multiphase flow regimes exist. Importantly, the improved mass and heat-exchange efficiency of hollow fiber membrane reactors suppress the formation of hot spots, temperature gradients, or accumulation of heat. Hollow fiber membrane reactors increase reaction selectivity and suppress byproduct formation, even for fast and highly exothermic reactions. The excellent heat- and mass-transfer characteristics of hollow fiber membrane reactors, together with the fact that the reaction is resolved along the length of the reaction channel, enables precise control of the residence time of intermediates or products, sometimes down to the microsecond level, by a thermal or chemical quench of the solution. However, the broadscale adoption of this technology has been limited due to the limited chemical and organic solvent resistance of commercial polymeric membrane systems.

Continuous-flow processes form the basis of the petrochemical and bulk chemicals industry, where strong competition, stringent environmental and safety regulations, and low-profit margins drive the need for high-performing, cost-effective, safe, and atom-efficient chemical operations. In contrast to the chemical industry, which produces commodity products, the fine-chemical industry primarily relies on its existing infrastructure of multipurpose batch or semi-batch reactors. Fine chemicals, such as drug substances and active pharmaceutical ingredients (APIs), are generally considerably more complex than commodity chemicals and usually require numerous, highly diverse reaction steps for their synthesis (typically 6 to 12 synthetic steps) as well as multiple rounds of quenching, separation, and purification. The adoption of hollow fiber membrane reactors for continuous-flow fine chemical production offers distinct advantages in virtually all phases of drug manufacturing, Bernhard Gutmann, David Cantillo, and C. Oliver Kappe, "Continuous-flow technology—A Tool for the Safe Manufacturing of Active Pharmaceutical Ingredients", Angewandte Review, Angew. Chem. Int. Ed., (2015), V. 54, pp. 6688-6728.

Liquid-liquid extraction (LLE) is an example of a selective transfer of molecules between two immiscible phases and is used extensively in chemical processes to transfer a solute dissolved in a first liquid to a second liquid that is essentially immiscible with the first liquid. The solution of the solute in the first liquid is generally termed a feed solution and the second liquid is termed an extractant or stripping liquid. The dissolved solute can be a solid, a liquid, or a gas. When the feed solution is brought into contact with the liquid extractant, the solute tends to distribute itself between the two liquids in accordance with the relative solubility of the solute in the two liquids. Since the feed solution and the liquid extractant are essentially immiscible, they form two distinct thermodynamic phases when in contact. These two phases can be physically separated from one another, which affects a separation of a fraction of the solute from the feed solution. In order to promote a rapid distribution of the solute between the feed solution and the extractant in conventional liquid-liquid extraction processes, the feed solution and the extractant are typically mixed together intimately to form a high interfacial surface area between the phases. The LLE process is carried out in mixer settler systems, column extractors, centrifugal extractors, and micro extractors. To promote efficient mixing and subsequent separation of the feed solution and extractant a number of column-type systems are evaluable. For example, KARR®, SCHEIBEL®, RDC®, and packed columns are available from Kock Modular Process Systems. However, such intimate mixing frequently gives rise to extensive problems. For example, the mixing of liquids forms a dispersion of one of the liquids in the other. The resultant dispersion can be stable so it takes a long time for the dispersed liquid to coalesce. As a result, the throughput of the solute-transfer process is undesirably low and the inventory of the feed solution and the extractant tied up in the process is undesirably high.

It has been recognized in the art that problems associated with conventional liquid-liquid extraction processes can be elevated by the use of porous membranes. U.S. Pat. No. 3,956,112 to Lee et al. refers to an extraction process in which a porous membrane serves as a partition between two immiscible solvents. Solutes from one solvent are transferred to the other solvent via direct solvent-solvent contact by the way of a porous membrane. The process includes the step of contacting the first side of the porous membrane with the feed solution containing the solute and contacting the second, opposing side of the membrane with the liquid extractant. The feed solution and the extractant can come into contact through the pores of the membrane. Within membrane pores, either the feed solution tends to displace the extractant or the extractant tends to displace the feed solution. The fluid which tends to displace the other defines a membrane-wetting liquid.

In liquid-liquid extraction with membrane contactors, the interface between phases is stabilized in a porous membrane that enables the transfer of compounds by diffusion in the membrane pores that are filled with one of the two liquids, without any phase mixing. The main benefits provided by the membrane-assisted extraction processes are as follows: the consecutive phase separation step (e.g., decantation, centrifugation) is no longer needed and the interfacial area between fluids at the membrane level remains constant regardless of operating flow rates and can be defined. However, the main drawbacks of this technology include a limited pressure range to ensure a stable interface between fluids, additional resistance to mass transfer, limited membrane stability in strong organic solvents, and limited membrane lifetime. The most widely used membrane contactors are made of polypropylene hollow fibers assembled into cartridges. Limited solvent resistance of polypropylene hollow fibers in strong organic solvents limits the wide application of this technology. Nevertheless, membrane contactors found utility in a range of applications, including in the selective recovery of organic acids, metals, proteins, and aroma compounds.

The ideal microporous membrane to facilitate solvent extraction should have the following characteristics:

1. Small-diameter pores to provide a stable interface at high cross membrane differential pressures even with relatively low interfacial tension systems as governed by the Young-Laplace equation;
2. The ability to impregnate ("wet") pores with fluid offering a higher level of solute solubility. see, for example U.S. Pat. No. 4,966,707;
3. Pore characteristics that minimize mass transfer resistance (e.g., high porosity and large diameter pores);
4. As thin a membrane as possible (i.e., membrane thickness) while maintaining sufficient physical strength.

Characteristics 1 and 3 are in conflict as related to pore size consideration. This conflict typically results in establishing a compromise pore size and porosity when using symmetric membranes. i.e., pores small enough to stabilize the interface, yet not too small to make membrane mass transfer resistance significant.

To decouple requirements 1 and 3, asymmetric porous membranes have been utilized. Single-skinned asymmetric membranes have been used in LLE processes with the small pores or the skinned side of the membrane used to immobilize the interface. The more open the interior and the alternate side of the membrane the lesser the membrane's resistance to mass transfer. The following references provide examples of the use of asymmetric membranes in LLE processes: R. Prasad et al. "Novel Liquid-In-Pore Configurations in Membrane Solvent Extraction", AIChE Journal, Vol. 36, (1990), p. 1592; A. M. Vaidya et al., "Aqueous-Organic Bioreactor. Part 1 A Guide to Membrane Selection", J. Mem. Sci., Vol. 71 (1992), p 139. It is also known to use dual-skinned asymmetric membranes for LLE. The use of dual-skinned asymmetric membranes for LLE is disclosed by K. K. Sirkar in U.S. Pat. No. 5,714,072.

The most common combination of solvents deployed in LLE is water and an organic solvent substantially immiscible in water. When the organic and the water-immiscible liquid phases containing a solute are brought into contact, the solute component "partitions" or "distributes" between the two layers. Once equilibrium is established, the ratio of the concentration of solute in each layer is constant for a given system and is represented by a value $m_i$ (designated as the partition coefficient or the distribution coefficient).

$$m_i = C_i^o / C_i^w$$

wherein $m_i$ is the distribution coefficient of solute i between organic and water phases, and $C_i^o$ and $C_i^w$ is the concentration of solute i in organic and water phases, respectively.

The liquid-liquid extraction can be carried between water and organic phase or between two organic phases, such as a polar and non-polar organic solvent, as long as phases are substantially immiscible. In the membrane-assisted non-dispersive liquid-liquid extraction process, the transfer of solute between the phases takes place through the wetted porous membrane. It is known in the art that for a very low $m_i$ system the overall mass transfer coefficient is higher for a hydrophilic membrane than for a hydrophobic membrane, while for a high value of $m_i$ the situation is reversed. For comparable boundary layer coefficients and membrane pore sizes, hydrophobic membranes are to be preferred for $m_i > 1$ systems, whereas hydrophilic membranes are preferable for $m_i < 1$ systems. Thus, both hydrophobic and hydrophilic porous membranes are needed. R. Prasad and K. K. Sirkar, "Dispersion-free extraction in microporous hollow fiber modules", AIChE Journal, Vol. 34 (1988), p. 177; R. Prasad and K. K. Sirkar, "Solvent extraction with microporous hydrophilic and composite membranes", AIChE Journal, Vol. 33 (1987), p. 1057;

The membrane-mediated LLE process has been used extensively for a range of chemical processes, including the recovery of pharmaceutical ingredients, biofuels, and metal ions. The membrane assisted LLE process provides significant advantages as compared to the conventional LLE process including:

1. no flooding limitations and hence the independent variation of individual phase flow rates;
2. no need for density differences between phases to aid phase separation by settling;
3. the ability to provide several extraction stages in a single piece of equipment as compared to a single-stage operation provided by mixer-settlers;
4. a very high interfacial area/unit equipment volume in well-packed hollow-fiber membrane units; and
5. the ability to handle systems that emulsify readily.

In membrane-mediated LLE, one fluid phase (phase 2) present on one side of the porous membrane occupies the pores of the membrane. The other immiscible fluid phase (phase 1) is on the other side of the membrane. The pressure of the fluid phase 1, $P_1$, must be equal to or greater than the pressure of the fluid phase 2, $P_2$, in order to immobilize the immiscible phase interface at the membrane pore mouth. However, $P_1$ must not exceed $P_2$ by an amount called $\Delta P_{critical}$; otherwise, the fluid phase 1 will break into the pore and will be dispersed into phase 2 as drops. As long as $P_1 \geq P_2$ but $P_1 - P_2 < \Delta P_{critical}$, phase interfaces are immobilized at the membrane pore mouths, no drops are formed in either phase and non-dispersive phase contacting-based separation is achieved.

The impregnation liquid wets the membrane pore structure and is kept in the pores by a capillary force. A critical displacement pressure is required for the non-wetting liquid to enter the pores and displace the wetting liquid. The critical displacement pressure as defined below is analogous to the maximum penetration pressure or the critical entry pressure. Displacement of the impregnating liquid by the non-wetting liquid occurs when the hydrostatic force exceeds the surface tension force holding the impregnating fluid in place. For a cylindrical capillary, the displacement pressure should be given by the "capillary pressure" relationship, known as the Laplace-Young equation, $$P_c = 2\gamma \cos \theta / r$$

where $\gamma$ is the interfacial tension, $\theta$ is the contact angle measured through the impregnating phase and $r$ is the capillary radius. A smaller pore radius increases the pressure requirement for the displacement of the impregnation liquid. However, the smaller size pores increase membrane resistance to the solute transport and can lead to a reduction in the transfer rate. The use of hollow fiber membranes that provide a high volumetric device surface area can alleviate or compensate for the decrease of the transport rate per unit of membrane area in membranes with small size pores.

Extraction processes in which immiscible solvents are separated by commercially available porous membranes frequently do not prevent one solvent from forming a dispersion in the other completely. Typically, one or the other of two solvents seeps through the porous membrane and becomes dispersed in the solvent on the other side of the membrane with time. As a result, conventional extraction processes involving immiscible solvents separated by a porous membrane generally must provide a settling tank and a solvent return mechanism to coalesce the dispersion formed by the seepage of one of the solvents through the membrane and to return the solvent thus recovered to its source. The phenomenon can be considered as a "break down" of the system, wherein the direct transport of liquids between the two phases separated by the membrane takes place. The deterioration of the liquid-liquid interface that leads to the formation of emulsions has been studied extensively. It has been demonstrated that initially, the surface shear forces due to stirring can be the main cause of liquid loss across the membrane leading to the formation of emulsions. Additional factors include surface shear forces, changes in surface tension, Marangoni effects, changes to membrane pore morphology, Benard instabilities, and membrane preparation protocol.

To stabilize the long-term performance and to prevent a solvent breakthrough, the use of stacked hydrophobic/hydrophilic membranes has been disclosed. R. Prasad and K. K. Sirkar, "Solvent extraction with microporous hydrophilic and composite membranes", AIChE Journal, Vol. 33 (1987), p. 1057. The composite stack consisted of hydrophilic cellulose acetate or Cuprophan film stacked on top of a hydrophobic Celgard™ or Goretex™ membrane. Each membrane in the stack is wetted by one phase only in the composite system, either aqueous or organic as the case may be; the aqueous-organic interface is at the interface of the hydrophilic and hydrophobic sections of the composite stack. It has been shown that the performances of these composites are unaffected by an excess phase pressure on either the aqueous or the organic side and there is no phase breakthrough regardless of the phase having an excess pressure. However, for a stacked composite membrane system there is an interfacial resistance between the two membranes due to a liquid film and tortuosity effects arising at the hydrophilic-hydrophobic interface inside the stacked composite membrane. The approach is limited to flat-sheet membrane configuration and the stacking approach cannot be applied to the preferred hollow fiber configuration.

K. K. Sirkar, in U.S. Pat. No. 4,997,569, discloses a method to control undesired seepage of solvents through the porous membrane. The process includes the step of maintaining an interface-immobilizing pressure difference between the feed solution and the extractant. The interface immobilizing pressure difference is imposed in a direction and a magnitude that is effective in substantially preventing the membrane-wetting liquid from flowing through the membrane and dispersing in the liquid on the opposite side of the membrane. The interface between the feed solution and the extractant is thereby effectively immobilized at the porous membrane. The interface-immobilizing pressure difference should be imposed in a direction to oppose the tendency of the membrane-wetting liquid to pass through the membrane. Thus, greater pressure is imposed on the liquid opposite to the membrane-wetting liquid in order to oppose the tendency of the membrane-wetting liquid to pass through the membrane. However, the method is difficult to implement in commercial hollow fiber devices. The range of differences in pressure effective to immobilize the interface between a particular feed solution and extractant for a particular porous membrane depends on a number of factors, including the relative tendency of the feed solution and the extractant to wet the membrane material, the interfacial tension between the feed solution and the extractant, the flow characteristics of each liquid at the surface of the membrane, and the effective diameters of the pores of the membrane. The minimum value of the pressure difference effective to immobilize the interface between the feed solution and the extractant at the porous membrane cannot in general be predicted a priori, largely because the formation of dispersion depends strongly on the pattern of flow of the liquids at the surface of the membrane. Pumping irregularities and pressure differences along the shell side and the bore side of hollow fiber devices make the determination of the average minimum pressure deference opposing the tendency of the membrane-wetting liquid to pass through the membrane exceedingly difficult. The change in the interfacial surface tension caused by compositional changes and membrane surface characteristics further compound the difficulty.

The maximum pressure difference across the impregnated porous membrane that the membrane can tolerate before the liquid "breakthrough" takes place is related to the membrane's maximum pore size and the pore structure, interfacial tension of fluids, and the contact angle. Once the critical pressure difference is exceeded, the impregnating liquid can be displaced out of that pore and the membrane fails to separate the phases. The available commercial membranes exhibit pore size in the microporous range, typically above 0.1 micron. However, due to a broad pore size distribution of commercially available membranes, larger pores contribute to an early "breakthrough". The commercial hydrophobic microporous membranes frequently undergo changes in pore morphology upon contact with aggressive solvent systems. When these changes are combined with a change in the interfacial surface tension, an early pore wet out occurs.

Porous membranes having defined wetting characteristics, hydrophobic or hydrophilic, are disclosed in the art for nondispersive membrane solvent extraction (MSX) where two immiscible phases flow on two sides of the membrane. The liquid-liquid interface across which solvent extraction/back extraction occurs remains immobilized on one surface of the membrane. This process requires the pressure of the phase not present in membrane pores to be either equal to or higher than that of the phase present in membrane pores. The excess phase pressure must not exceed a breakthrough pressure. During countercurrent membrane solvent extraction processes with significant liquid flows, a pressure drop in each phase will be present: this often causes the liquid breakthrough. Real-world high surface area membrane devices, such as hollow fiber devices, typically generate pressure drops as fluids are transported. Thus, a pressure drop will exist from one side to the opposite side of the membrane in a commercial device. This can lead to one phase intrusion into another. To overcome this problem, flat porous Janus membranes were developed, one side of which is hydrophobic and the other being hydrophilic. Preparation and use of such membranes for non-dispersive solvent extraction is described by Lydia N. Rodrigues, et al., in "Porous hydrophobic-hydrophilic Janus membranes for nondispersive membrane solvent extraction", Journal of Membrane Science, (2021), V. 637, 119633. Nondispersive solvent extractions were carried out successfully using either polypropylene (PP) based or polyvinylidene fluoride (PVDF) based or polyamide (Nylon) based membranes one side of which was hydrophobic and the other side being hydrophilic. Thus, the potential practical utility of the MSX technique can be substantially enhanced via Janus MSX membrane utilization.

It is known to carry membrane-based gas and liquid separations using porous membranes in the form of supported liquid membranes. Supported liquid membranes (SLMs) provide a selective separation technique for liquid and gas systems. A major limitation of SLM technology is the tendency to membrane instability, where displacement and loss of liquid inventory occurs. One cause of instability is the transmembrane pressure across the membrane caused by the pumping of fluids. A number of solutions have been proposed to improve the stability of SLMs. W. S. Winston Ho, in U.S. Pat. No. 6,433,163, discloses a combined supported liquid/strip dispersion process. The loss of liquid membrane inventory is continuously or periodically rejuvenated by a strip dispersion. The process improves SLM stability but forms stable emulsions. Thus, a need still exists in developing commercially viable SLMs Preparation of improved liquid-based microscale porous (LBMP) systems based on dynamic liquid-liquid interfaces has been recently described by Zhecun Wang, et al., "A liquid-based Janus porous membrane for convenient liquid-liquid extraction and immiscible oil/water separation", Chem. Communications, (2019), V. 55, p. 14486. The Janus porous polypropylene-based membrane, JPM, with a superimposed hydrophilic surface layer is hydrophobic-oleophilic on one side and hydrophilic-underwater oleophobic on the other side. Thus, the membrane consists of simultaneously infused water and organic solvents, and it also gates the organic solvents and water at the same time exhibiting the "self-gating" behavior.

A range of materials is used to form porous membranes used in membrane contactor and membrane-assisted LLE processes. Inorganic and polymeric materials have been used for porous membrane preparation. Polymeric materials are preferred since they allow the preparation of small-diameter hollow fibers. To enable contact with aggressive organic liquids, good solvent resistance is a prerequisite for use of polymeric membranes. The membrane must further exhibit a uniform small pore structure combined with high pore volume to meet additional process criteria. To date, membrane materials used in these processes have been largely limited to polypropylene, Teflon™, polyvinylidene fluoride, and cellulose and its derivatives. None of the hollow fiber membranes made from these materials exhibits the prerequisite optimal combination of pore morphology and solvent resistance. In particular, the need exists for solvent-resistant hollow fiber membranes with a mesoporous pore structure.

Poly (aryl ether ketone)s, PAEKs, represent a class of semi-crystalline engineering thermoplastics with outstanding thermal properties and good solvent and chemical resistance. One of the representative polymers in this class is poly (ether ether ketone), PEEK, which has a reported continuous service temperature of approximately 250° C. PAEK polymers are virtually insoluble in all common solvents at room temperature. These properties make PAEK attractive materials for porous membrane preparation. However, the intractability of PAEK makes the preparation of membranes with controlled porosity exceedingly difficult. Current membrane substrate media is prepared by solution-based processes. Semi-crystalline PAEK materials are insoluble in common solvents. PAEK polymers can be chemically modified to impart solubility, for example, by sulfonation. However, articles formed from such functionalized PAEK polymers lose many of the desired properties. Bulk modification leads to a disruption in the ability of the polymer chain to crystallize and articles subsequently formed from such functionalized polymers lose solvent resistance and much of their thermo-mechanical properties.

Preparation of porous materials from poly (aryl ether ketones), PAEKs, has been largely limited to the PAEK family member poly (ether ether ketone), PEEK. Furthermore, the development of porous PEEK membrane materials was limited to gas separation membranes and liquid filtration membranes, exclusively. A number of methods to prepare porous PEEK membranes have been disclosed in the art. It is known to prepare porous PEEK membranes from solutions of strong acids, such as concentrated sulfuric acid. However, PEEK can undergo sulfonation in the concentrated sulfuric acid media and thus can lose some of its desirable sought-after properties. U.S. Pat. No. 6,017,455 discloses the preparation of non-sulfonated porous PEEK membranes from concentrated sulfuric acid solvents sufficiently diluted by water to prevent sulfonation. The membranes are formed by casting a PEEK solution to form a film followed by coagulation in concentrated sulfuric acid. This membrane preparation process is complicated and produces large amounts of waste acid.

U.S. Pat. No. 5,997,741 discloses the preparation of porous PEEK membranes by forming a solution of PEEK polymer in a concentrated sulfuric acid at a temperature of 15° C. or lower to prevent sulfonation. The solution is processed and cast at a sub-ambient temperature, followed by coagulation in water or in concentrated sulfuric acid. Only dilute PEEK solutions can be formed in the concentrated sulfuric acid, which adversely affects film-forming characteristics, the mechanical characteristics, and the pore morphology of the thus formed porous PEEK membranes.

U.S. Pat. Nos. 4,992,485 and 5,089,192 disclose the preparation of porous PEEK membranes from non-sulfonating acid solvents, which include methane sulfonic acid and trifluoromethane sulfonic acid. European Patent Specification EP 0737506 discloses the preparation of improved polymeric membranes based on PEEK admixtures with polyethylene terephthalate. The membranes are formed by the solution casting process from a methane sulfuric acid/sulfuric acid solvent mixture.

Tao Huang and coworkers prepared flat sheet porous PEEK membranes via immersion precipitation using a solvent mixture consisting of methanesulphonic acid and sulfuric acid. Reference Tao Huang et al., "Enabling sustainable green close-loop membrane lithium extraction by acid and solvent resistant poly (ether ether ketone) membrane", J. Mem. Sci., Vol. 589, (2019), p. 117273. Successful stripping of lithium ions from the lithium-loaded extractant using concentrated HCl solution was demonstrated. The PEEK membrane showed good long-term stability in HCl solution and in organic extractant (tributyl phosphate (TBP)/kerosene).

The acid-based solvent systems for the manufacture of porous PEEK membranes disclosed in the art are highly corrosive, frequently toxic, and generate substantial environmental and disposal problems. For these and other reasons, the acid-based casting processes have found limited commercial use.

An alternative to the acid-based solvent system for PEEK membrane preparation involves the use of high boiling point solvents and plasticizers that dissolve PEEK polymer at elevated temperatures. U.S. Pat. Nos. 4,957,817 and 5,064,580, both issued to Dow Chemical Co., disclose the preparation of porous PEEK articles from its admixture with organic polar solvents having a boiling point in the range of 191° C. to 380° C., such as benzophenone and 1-chloronaphthalene, and organic plasticizers capable of dissolving at least 10 weight percent of PEEK, respectively. The final porous article is formed by removing the organic polar solvents and/or plasticizers by dissolution into a low boiling temperature solvent. U.S. Pat. No. 5,200,078 discloses the preparation of microporous PEEK membranes from its mixtures with plasticizers wherein the membrane undergoes a drawing step prior to or after the plasticizer is removed by leaching. U.S. Pat. No. 5,227,101 issued to Dow Chemical Co. discloses the preparation of microporous membranes from poly (aryl ether ketone) type polymer by forming a mixture of PEEK type polymer, a low melting point crystallizable polymer, and a plasticizer, heating the resulting mixture, extruding or casting the mixture into a membrane, quenching or coagulating the membrane and leaching the pore-forming components. U.S. Pat. No. 5,205,968, issued to Dow Chemical Co., discloses the preparation of microporous membranes from a blend containing a poly (aryl ether ketone) type polymer, an amorphous polymer, and a solvent.

M. F. Sonnenschein in the article entitled "Hollow fiber microfiltration membranes from poly (ether ether ketone)", published in the Journal of Applied Polymer Science, Volume 72, pages 175-181, 1999, describes the preparation of PEEK hollow fiber membranes by a thermal phase inversion process. The use of a leachable additive polymer, such as polysulfone, is proposed to enhance membrane performance. Preparation of porous PEEK membranes by coextrusion of PEEK with polysulfone polymers followed by the dissolution of the polysulfone polymer from the interpenetrating network is disclosed in European Patent Application 409416 A2.

It is also known in the art to prepare porous PEEK membranes from its blends with a compatible poly (ether imide) polymer, PEI. Preparation of such membranes is described by R. S. Dubrow and M. F. Froix in U.S. Pat. No. 4,721,732 and by R. H. Mehta et al. in an article entitled "Microporous membranes based on poly (ether ether ketone) via thermally induced phase separation", published in the Journal of Membrane Science, Volume 107, pages 93-106, 1995. The porous structure of these PEEK membranes is formed by leaching the poly (ether imide) component with an appropriate strong solvent, such as dimethylformamide. However, as described by Mehta et al., the quantitative removal of PEI components by leaching is essentially impossible which in turn can lead to an inferior porous structure.

Japan Kokai Tokkyo Koho 91273038 assigned to Sumitomo Electric Industries, Ltd., discloses the preparation of porous PEEK membranes by an ion track etching method.

M. L. Bailey et al., in U.S. Pat. No. 5,651,931, describe a sintering process for the preparation of biocompatible filters, including PEEK filters. The filters are formed from a PEEK powder of pre-selected average particle size by first pressing the powder into a "cake" followed by sintering in an oven or furnace. The process is limited to the preparation of filters with a relatively large pore size and a broad pore size distribution and does not provide economic means of forming large membrane area fluid separation devices.

A process for the preparation of porous PAEK articles that preserves the desirable thermal and chemical characteristics of PAEK polymers has been disclosed in U.S. Pat. No. 6,887,408. The porous articles are prepared from PAEK blends with compatible polyimides. An article of targeted shape is formed from the PAEK/polyimide blend by melt processing followed by removal of the polyimide phase by reaction with a primary amine. The method enables the preparation of shaped porous PEEK articles, including hollow fiber membranes. Preparation of such hollow fiber membranes is described by Yong Ding and Ben Bikson in the article entitled "Preparation and characterization of semi-crystalline poly (ether ether ketone) hollow fiber membranes", published in the Journal of Membrane Science, volume 357 (2010), p. 192-198. Preparation of hollow fiber membranes by this methodology is further described by Gong Chen, Yuan Chen, Tingjian Huang, Zhongchen He, Jianjun Xu, and Pengqing Liu, in the article entitled "Pore Structure and Properties of PEEK Hollow Fiber Membranes: Influence of the Phase Structure Evolution of PEEK/PEI Composite", Polymers, Volume 11 (2019), p. 1398.

D. Morrisette and P. Croteu, in PCT application, International Publication No. WO 2007/051309, disclose porous PEEK material suitable for medical implant devices. The porous material is formed by mixing dissolvable material with PEEK in a molten form and subsequently removing the dissolvable material. The disclosed dissolvable material is salt. The method is capable of forming PEEK materials with very large pore size and irregular pore structure.

M. C. Iliuta et al., in U.S. Pat. No. 9,908,985, disclose the preparation of microporous hydrophobic polymeric hollow fibers. The hollow fibers are prepared by melt processing from a mixture of polymer with micron-size NaCl particles followed by salt dissolution. The hollow fiber is reported to be non-wetting and useful for gas transfer contacting applications.

Poly (aryl ether ketone)s are high-performance engineering polymers that exhibit exceptional thermal and chemical characteristics and are thus highly sought after as porous substrates for applications that require solvent and thermal resistance. However, the properties that make PAEK polymers desirable also make the preparation of porous media difficult. In contrast, the chemical resistance of PAEK polymers enables the chemical modification of preformed polymer surfaces without alteration of the underlying structure.

A number of techniques have been used in the art to chemically modify the surface of dense PEEK materials to affect surface characteristics, such as friction, wettability, adsorption, and adhesion, including cell adhesion. O. Noiset, et al., have modified the PEEK film surface using wet-chemistry technique by selectively reducing ketone groups to form hydroxyl groups (Macromolecules, volume 30, p. 540-548, 1997) and then covalently fixing hexamethylene diisocyanate by addition onto the hydroxyl function (Journal of Polymer Science, Part A, Vol. 35, pages 3779-3790, 1997). The hexamethylene diisocyanate modified PEEK film was subsequently modified to attach amines and amino acids, thus modifying the film surface to be used for cell growth.

C. Henneuse-Boxus, et al., have modified PEEK film surfaces using photochemical routes (European polymer Journal, Vol. 37, pages 9-18, 2001) and attached fluorescent probes to PEEK film surfaces (Polymer, Vol 41, pages 2339-2348, 2000). P. Laurens, et al., have modified PEEK surfaces with excimer laser radiation (Applied Surface Science, Vol. 138-139, pages 93-96, 1999). N. Frauchina and T. McCarthy have modified semi-crystalline PEEK films with carbonyl-selective reagents to induce surface functionality (Macromolecules, Vol. 24, pages 3045-3049, 1991). The surface-modified films were robust and unaffected by a variety of solvents. In U.S. Pat. No. 5,260,415, I. David disclosed a process for the crosslinking of polymer containing diaryl ketone groups by heating the polymer with alcohol and/or alkoxide to enhance chemical resistance.

Preparation of composite perfluoro-hydrocarbon membranes by surface modification and surface coating of porous PEEK is disclosed in U.S. Pat. Nos. 9,610,547 and 10,376, 846. The super-hydrophobic properties of disclosed membranes enable a range of gas and vapor separations. Preparation of surface-functionalized porous PEEK materials is disclosed in U.S. Pat. No. 7,176,273. Tailored functionalization imparted hydrophilic or hydrophobic properties to the material. The use of thus functionalized PEEK materials for membrane gas separation and nanofiltration has been further disclosed.

The use of porous polymeric hollow fibers, such as polypropylene hollow fibers, as membrane contactors for a range of contactor applications, including for liquid-liquid extraction applications, has been disclosed in the art. Nevertheless, the limited solvent stability in numerous specific applications, and interface stabilization between fluids in the membrane, required to avoid emulsions, still represent a challenge. Poly (aryl ether ketone) hollow fibers exhibit improved solvent resistance. The use of porous poly (aryl ether ketone) hollow fibers as membrane contactors for molecular transfer between phases including in liquid-liquid extraction applications is unknown.

It was found surprisingly that mesoporous poly (aryl ether ketone) hollow fibers enable the efficient transfer of molecules into fluid reactive media, removing reaction products from fluid reaction media, and stable liquid-liquid extractions. The porous hollow fibers formed from semi-crystalline poly (aryl ether ketones) are highly stable in aggressive organic solvents and can be functionalized heterogeneously to form membranes with tailored hydrophobic or hydrophilic surface characteristics. A novel method of forming porous poly (aryl ether ketone) membranes with alternating hydrophobic and hydrophilic layers within the membrane wall is further disclosed.

SUMMARY OF THE INVENTION

Many industrially important chemical transformations involve molecular transfer between multiple phases (gas-liquid, solid-liquid, liquid-liquid, or solid-liquid-gas). In multi-phase chemical processes, efficient transfer of molecules between the phases is necessary for an efficient generation of reaction products with reduced byproduct formation. The method of the present invention provides for a controlled transfer of molecules between gas-liquid and liquid-liquid phases and is characterized by the use of a porous poly (aryl ether ketone) membrane, PAEK, that serves as a partition between the phases. The porous membrane can be in the form of a flat sheet or a hollow fiber. In the preferred embodiment, the porous PAEK membrane is a mesoporous hollow fiber membrane.

In its broadest embodiment, the method of the invention entails the transfer of at least one molecule from a first phase into a second phase across a porous poly (aryl ether ketone) hollow fiber membrane, wherein no transfer of the first phase into the second phase takes place. Thus, the transfer of molecules between the phases takes place without phase intermixing even under conditions wherein a pressure differential can exist between the phases.

The first phase can be a gas and the second phase a liquid. A gaseous reactant is transferred in a controlled manner into the reaction media and/or gaseous products or byproducts are removed from the reaction media via a porous PAEK membrane. For example, oxygen in an oxygen-containing gas is transferred across a porous PAEK hollow fiber membrane into liquid reaction media to affect the oxidation reaction. In another example, the carbon dioxide is removed from the reaction media continuously via a porous PAEK membrane. The gas phase and the liquid phase come into contact through the pores of the membrane. Within membrane pores, the gas phase tends to displace the liquid phase. The transfer of a gas molecule between the gas and the liquid phase can be non-reactive as well and governed by Henry's solubility constant. $C = k \cdot P$, wherein C is the concentration of the dissolved gas, k is Henry's constant, and P is the partial pressure of the gas. It is also within the scope of the invention to transfer gas molecules from one gas to a second gas via a liquid phase wherein the liquid phase is retained within a porous poly (aryl ether ketone) membrane.

In some embodiments of the invention, the first and the second phases are both liquids. A solute or solutes from one liquid are transferred into another liquid via direct liquid-liquid contact by the way of the porous PAEK membrane. The membrane device serves as a membrane reactor in some embodiments, while in other embodiments the membrane device serves as a liquid-liquid extractor. The solute is transferred into a reaction media or is removed from the reaction media via the porous PAEK membrane wherein the transfer of molecules between the phases takes place without phase intermixing even under conditions wherein a pressure differential can exist between the phases The process includes the step of contacting the first side of the porous membrane with the feed solution containing the solute and contacting the second, opposing side of the membrane with the liquid extractant. The feed solution and the extractant come into contact through the pores of the membrane. Within membrane pores, either the feed solution tends to displace the extractant liquid or the extractant tends to displace the feed solution. The fluid which tends to displace the other defines a membrane-wetting liquid.

In multi-phase chemical processes, efficient transfer of molecules between the phases is necessary for selective generation of reaction products with reduced byproduct formation. Conventional batch or semi-batch reactor-based processes can suffer from poor mass and heat transfer due to small surface-to-volume ratios. Interface mixing in large commercial scale batch reactors continues to present challenges and can suffer from the formation of localized hot spots in exothermic reactions leading to safety concerns. The rate of mass transfer is important in biphasic systems, where the overall reaction rate is affected by the rate of transfer of active species between the two phases. Continuous flow membrane reactors have the potential to mitigate challenges (including safety challenges) associated with using batch reactors by enabling the controlled introduction of reactants into the reaction media and controlled removal of products or byproducts from the reaction media. Furthermore, the membrane-assisted molecular transfer between the phases can take place with or without phase intermixing and selectively or non-selectively. The molecular transfer between the phases can be carried out to affect and control a chemical reaction (i.e., utilizing a membrane device as a chemical reactor), to separate individual components from a reaction mixture (i.e., utilizing a membrane device as a stand-alone separator), or as a combined membrane/reaction product separator in a single device. The chemically solvent-resistant mesoporous PAEK hollow fiber membranes were found to be particularly effective in facilitating an efficient transfer of molecules between phases.

The invention discloses the preparation of porous poly (aryl ether ketone) hollow fiber membranes that enable the efficient transfer of molecules between phases and the use thereof for processes involving the transfer of molecules between phases. More particularly, the teachings of the present invention are directed to the preparation of solvent-resistant mesoporous poly (aryl ether ketone) hollow fiber membranes that enable processes of molecular transfer between the phases under conditions of differential pressure between the phases without intermixing. The poly (aryl ether ketone) hollow fibers of this invention are semi-crystalline and exhibit a Janus-like structure with a combination of hydrophilic and hydrophobic surface characteristics. Preparation of stable supported liquid membranes (SLM) utilizing mesoporous poly (aryl ether ketone) hollow fibers to enable the efficient selective transfer of molecules between the phases is further disclosed. Structured hollow fiber devices constructed utilizing poly (aryl ether ketone) hollow fibers provide efficient molecular mass transfer between the phases without phase intermixing, including liquid-liquid extraction processes.

The mesoporous PAEK hollow fiber membranes are particularly effective in solute transfer in membrane-assisted liquid-liquid extraction processes. The membrane-assisted liquid-liquid extraction processes are enabled by porous poly (aryl ether ketone) hollow fiber membranes, PAEK, with controlled hydrophilic or hydrophobic surface characteristics. Also disclosed is the preparation of mesoporous Janus-like poly (aryl ether ketone) hollow fiber membranes with alternating hydrophobic and hydrophilic surfaces and their use for liquid-liquid extraction processes. Based on the interaction between the two immiscible liquids and different surfaces of the Janus membrane, a novel dynamic liquid-based Janus porous PAEK membrane system is formed. Some desirable characteristics of the Janus membrane are self-gating, enabling stable continuous liquid-liquid extraction without phase intermixing even wherein a differential pressure between the phases exists.

The extraction processes of the instant invention are characterized by the use of a porous PAEK membrane that serves as a partition between two immiscible solvents. The most common combination of solvents is water and a non-polar organic solvent; a combination of a polar organic solvent immiscible with a non-polar organic solvent is further utilized. The porous membrane can be in the form of a flat sheet or a hollow fiber. In the preferred embodiment, the porous PAEK membrane is a mesoporous hollow fiber membrane. Solutes from one solvent are transferred to the other solvent via direct solvent-solvent contact by the way of the porous PAEK membrane. The process includes the step of contacting the first side of the porous membrane with the feed solution containing the solute and contacting the second, opposing side of the membrane with the liquid extractant. The feed solution and the extractant can come into contact through the pores of the membrane. Within membrane pores, either the feed solution tends to displace the extractant liquid or the extractant tends to displace the feed solution. The fluid which tends to displace the other defines a membrane-wetting liquid.

Porous membranes used in liquid-liquid extraction processes of this invention are comprised of poly (aryl ether ketone), PAEK, polymers. The porous PAEK membranes exhibit a uniform, narrow pore size distribution. The pore size is substantially within the mesoporous size range. A mesoporous material is a material containing pores with diameters between 2 and 50 nm, according to the International Union of Pure and Applied Chemistry, IUPAC, nomenclature. For comparison, IUPAC defines microporous material as a material having pores smaller than 2 nm in diameter and macroporous material as a material having pores larger than 50 nm in diameter. The porous materials of this invention exhibit an average pore diameter between 5 and 100 nm, which is defined herein as being substantially mesoporous or nanoporous. In some embodiments of this invention, the porous structure of the PAEK article is comprised of structural segments that differ in pore size; this includes porous materials comprised of two or more layers of different pore sizes. The layers can contain mesopores that differ in pore size or the article can be comprised of mesoporous and macroporous layers. It is further within the scope of this invention to form materials with bimodal pore distribution that contain mesopores and macropores.

The mesoporous membranes used in the methods of the present invention are formed from poly (aryl ether ketone)

polymers, PAEK. The porous poly (aryl ether ketone) polymers are defined as polymers containing at least one repeat aryl ether ketone segment in the polymeric backbone. A number of poly (aryl ether ketone) polymers are available commercially including poly (ether ketone), poly (ether ether ketone), poly (ether ketone ketone), poly (ether ether ketone ketone), poly (ether ketone ether ketone ketone) and copolymers collectively referred herein as poly (aryl ether ketones). Poly (aryl ether ketones) have a weight average molecular weight in the range of 20,000 to 1,000,000 Daltons, typically between 30,000 to 500,000 Daltons. Preferred poly (aryl ether ketones) used to form porous PAEK membranes of this invention are semi-crystalline and are insoluble in common organic solvents at room temperature. Most preferred poly (aryl ether ketones) used to form porous PAEK articles of this invention are poly (ether ether ketone), PEEK, poly (ether ketone), PEK, poly (ether ketone ketone), PEKK, poly (ether ether ketone ketone), PEEKK, and poly (ether ketone ether ketone ketone), PEKEKK. A number of poly (aryl ether ketones) are manufactured by Victrex Corporation under the trade names Victrex® PEEK, Victrex® PEEK HT, and Victrex® PEEK ST. Poly (ether ether ketone) is further available from Solvay under the trade name KetaSpire™ and another poly (aryl ether ketone) is available from Solvay under the trade name AvaSpire®. Poly (ether ether ketone) is further available from Evonik Corporation under the trade name VESTAKEEP®.

The PAEK membranes used in liquid-liquid extraction processes of this invention can be in a flat sheet configuration or in a hollow fiber (microcapillary) configuration, wherein both membrane configurations exhibit a mesoporous pore structure with a narrow pore size distribution and an average surface pore size between 5 and 100 nanometers. The membrane is preferably shaped as a hollow fiber. In some embodiments, the mesoporous wall structure exhibits a bimodal pore size distribution. The bimodal distribution consists of a mesoporous pore fraction with an average pore size below 100 nanometer and a macro-porous pore fraction with an average pore size above 0.5 micron. It is also within the scope of the present invention to utilize porous PAEK hollow fibers for LLE applications with asymmetric or a combination of asymmetric and multi-layer pore wall morphology. Hollow fibers with graded pore structure comprised of a thin mesoporous surface layer and macro-porous bulk wall structure exhibit higher solute mass transfer rates while maintaining good stability. Hollow fibers with the layered graded pore structure are formed by coextrusion processes from membrane forming compositions with different contents of pore-forming materials. It is also within the scope of the invention to utilize hollow fibers with the asymmetric wall pore structure, wherein the mesoporous smaller pore size layer is located at both the external and the lumen side of the hollow fiber.

Mesoporous poly (aryl ketone) hollow fibers used to conduct LLE processes of this invention are prepared via a multi-step process. A solid (non-porous) precursor micro-capillary of the desired dimensions is formed first from a PAEK polymer blend with a pore-forming material by melt processing. In the preferred embodiment, the pore-forming material is a polyimide. The precursor solid micro-capillary is subjected to a post-processing step to maximize the degree of crystallinity of the PAEK phase. In the following step, the micro-capillary article is converted into a mesoporous material by removing the pore-forming material. If the polyimide is used as a pore-forming material, the removal is affected by chemically decomposing the polyimide and removing the decomposition products to form the thus formed mesoporous material. The reaction conditions during the polyimide's decomposition and removal are maintained to form alternatively a hydrophilic or a hydrophobic pore surface. The surface of the porous hollow fiber can be further chemically modified with hydrophilic or hydrophobic functional groups tailored towards a specific LLE process in a follow-up step. The chemical functionalization can be a multi-step process to form the surface chemistry most optimal for a specific LLE process.

Porous poly (aryl ketone) hollow fibers with hydrophilic surface characteristics are preferred for LLE processes wherein the solute distribution coefficient $m_i$ is low. The use of hydrophilic hollow fibers in such systems provides for a higher overall mass transfer coefficient. Porous poly (aryl ketone) hollow fibers with hydrophobic surface characteristics are preferred for LLE processes wherein the solute distribution coefficient $m_i$ is high. For comparable boundary layer coefficients and membrane pore sizes, hydrophobic membranes are to be preferred for $m_i>1$ systems, whereas hydrophilic membranes are preferable for $m_i<1$ systems.

In preferred embodiments of this invention, the hydrophilic and hydrophobic membrane surfaces are formed by a wet-chemical surface modification of the pre-formed porous PAEK membrane, including the Janus PAEK membranes that exhibit an alternating hydrophilic/hydrophobic surface. To form the hydrophilic surface, the porous material is modified with hydroxyl groups, ethylene oxide groups, primary, secondary, tertiary or quaternary amino groups, carboxylic acid groups or sulfonic acid groups, among others. Ethylene oxide and hydroxyl groups are particularly preferred for the hydrophilization of the preformed PAEK hollow fiber surface. The natural surface characteristics of porous poly (aryl ether ketone) membranes are substantially hydrophobic. The hydrophobic characteristics of PAEK membranes can be amplified further by surface modification with hydrophobic functional groups, such as linear hydrocarbons and silicon groups. However, modification of mesoporous surfaces with perfluoro hydrocarbon groups and oleophobic silicon groups can lead to the formation of a superhydrophobic surface, i.e., a "Lotus effect" phenomenon. Superhydrophobic surfaces exhibit non-wetting characteristics even for non-polar organic liquids. Membranes with superhydrophobic properties may thus become inapplicable for LLE applications.

The invention discloses an efficient method of transferring at least one molecule from a first phase into a second phase across a porous poly (aryl ether ketone) hollow fiber membrane, wherein the transfer of the molecule from the first phase into the second phase takes place under conditions that a pressure differential exists between the phases without phase intermixing. The differential pressure can exceed 10 psig (68 kPa) and in some embodiments 50 psig (245 kPa) without a phase breakthrough across the membrane. In one embodiment, the first phase is a gas and the second phase is a liquid. In another embodiment, the first phase and the second phase are liquids. It is further within the scope of the invention to transfer a gas molecule between two gas phases through a porous poly (aryl ether ketone) hollow fiber membrane impregnated with a liquid. The molecule can be a reactant transferred from the first phase into the second phase or a reaction product removed from the first phase into the second phase. Thus, the poly (aryl ether ketone) hollow fiber membrane functions as a membrane reactor.

In preferred embodiments, the porous hollow fiber membrane has an asymmetric pore structure with a mesoporous surface layer containing smaller size pores than an interior portion of the porous hollow fiber membrane wall. The asymmetric pore structure provides for an improved mass transfer rate while still preventing cross-membrane phase breakthrough. The mesoporous surface of the poly (aryl ether ketone) hollow fiber membrane can be hydrophobic or hydrophilic. It is further advantageous to deploy a poly (aryl ether ketone) hollow fiber membrane that exhibits a Janus porous structure constructed of alternating layers with hydrophilic and hydrophobic surfaces.

In some embodiments, the porous poly(aryl ether ketone) membrane surface-functionalized with hydrophilic groups is prepared by the process comprising: (a) forming a blend of poly(aryl ether ketone) polymer with a polyimide; (b) forming a shaped hollow fiber from the blend by extrusion; (c) crystallizing the poly (aryl ether ketone) phase in the hollow fiber; (d) forming a porous structure throughout hollow fiber wall, while simultaneously functionalizing the surface of the wall by bringing the hollow fiber into contact with a primary amine to simultaneously decompose the polyimide in the shaped hollow fiber into low molecular weight fragments and to functionalize membrane surface with ketimine groups, and (e) removing the low molecular weight fragments from the hollow fiber.

In preferred embodiments, the porous poly (aryl ether ketone) hollow fiber membranes have tailored hydrophilic or hydrophobic surface properties. The surface functionalization is conveniently carried out on the preformed porous poly (aryl ether ketone) hollow fiber membranes of optimized pore morphology. An asymmetric pore morphology is preferred. The poly (aryl ether ketone) hollow fibers exhibit exceptional solvent and chemical resistance and high-temperature thermal stability. These characteristics enable surface modification of the preformed porous PAEK hollow fibers without affecting pore structure. Thus, the porous poly (aryl ether ketone) hollow fiber membranes used to conduct molecular transfer processes are prepared by a method comprising: (a) forming a blend of poly (aryl ether ketone) type polymer with a pore-forming material; (b) forming a non-porous (dense) micro-capillary of desired dimensions from the blend by extrusion; (c) crystallizing the poly (aryl ether ketone) phase in the shaped article; and (d) removing the pore-forming material to form porous PAEK hollow fiber. The porous PAEK substrate formed by the above-described process is functionalized in a subsequent step with target surface groups to form hydrophobic or hydrophilic porous PAEK hollow fibers. The thus formed porous hollow fiber membranes are incorporated into a fluid separation device. In some embodiments, the functionalization of the porous PAEK membrane is carried out in-situ in the preformed fluid separation device. The preferred pore-forming additives are polyimides and the most preferred polyimide is polyetherimide.

The preformed poly (aryl ether ketone) hollow fibers can be fabricated with a homogeneous, asymmetric or layered pore structure. By controlling the original blend composition, extrusion process conditions by which the micro-capillary is formed and the crystallization protocol, porous hollow fibers with asymmetric or layered pore structure can be formed. Two or more poly (aryl ether ketone)/polyimide blends of different blend compositions can be formed in step (a) and coextruded in step (b) to form a micro-capillary with a variable layered wall composition. Upon polyimide phase extraction, the capillary formed by coextrusion will have a different pore size in each layer. The crystallization protocol in step (c) affects PAEK crystal size which, in turn, affects the pore size of the wall layer upon removal of the polyimide phase. Thus, the porous wall structure in these embodiments can be homogeneous, asymmetric or multi-layer composite.

The surface functionality of hollow fibers that have been fabricated with the predetermined homogeneous, asymmetric or multi-layer composite pore structure can be identical throughout porous wall cross-sections and can be hydrophilic or hydrophobic. Alternatively, the porous wall can exhibit a layered porous wall structure with alternating hydrophilic and hydrophobic regions, respectively.

In another preferred embodiment of the present invention, the poly (aryl ether ketone) membrane with a layered porous wall structure, wherein each layer carries a different surface functionality, is used to carry out liquid-liquid extraction processes. The wall of the porous poly (aryl ether ketone) membrane is formed with alternating hydrophilic and hydrophobic layers. To form the layered structure, the dense wall of the shaped precursor (micro-capillary or flat sheet) is etched to a predetermined depth from one side only, while maintaining the adjacent dense region intact; the thus formed porous section of the wall formed by the etching process is functionalized with hydrophilic groups; the article is subjected to further etching to form a porous structure in the previously unaffected dense section; the second etching step is carried out under conditions that preclude modification of the porous wall with hydrophilic groups. By controlling the etching process conditions during the initial etching step (the temperature and the etching reagent concentration), as well as the duration of the etching step, the initial porous layer of desired thickness is formed. The thickness of the second layer in the membrane wall is thus predetermined by the thickness of the initial porous layer. Thus, a layered porous wall structure is formed with interconnected hydrophilic and hydrophobic segments of predetermined thicknesses. Water-based liquid tends to wet-out the hydrophilic porous layer while organic liquid tends to wet-out the hydrophobic porous layer. The feed solution and the extractant thus come into contact through the hydrophilic and the hydrophobic layer within the porous wall of the membrane enabling an efficient solute transfer.

More specifically, the hollow fiber membrane with alternating adjacent hydrophilic and hydrophobic layers is prepared by a method comprising: (a) forming a blend of poly(aryl ether ketone) type polymer with a polyimide; (b) forming a shaped micro-capillary from the blend by extrusion; (c) crystallizing the poly (aryl ether ketone) phase in the shaped article; (d) bringing one side of the micro-capillary (external or internal) into contact with a primary amine for a predetermined period of time to affect decomposition of the polyimide in the exposed wall to a predetermined depth while maintaining the unexposed portion of the wall thickness intact; (e) removing the low molecular weight fragments from the etched wall segment; (f) functionalizing the thus formed porous segment of the wall with hydrophilic groups; (g) bringing the micro-capillary into contact with a primary amine to affect decomposition of the polyimide in the remaining dense section of the wall; and (h) removing the low molecular weight fragments from the etched porous wall segment. The decomposition of the polyimide into low molecular weight fragments during steps (d) and (g) is carried out under conditions that do not cause functionalization of the membrane surface with the primary amine. Advantageously, the membrane is washed and dried following each etching step. The thus formed porous membranes are incorporated into a fluid separation device. In some embodiments steps (d) through (h) are carried out in-situ in the preformed fluid separation device comprised of micro-capillaries.

By controlling the original blend composition in step (a), extrusion process conditions by which the micro-capillary is formed in step (b), and the crystallization protocol in step (c), porous hollow fibers with asymmetric or layered pore structure can be formed following polyimide phase removal. In these embodiments, the wall pore structure formed following the removal of the polyimide phase is structurally non-homogeneous. Layers throughout the wall thickness exhibit different pore sizes due to differences in PAEK/polyimide blend ratio and PAEK crystal size in each layer. By carrying out steps (d) through (h) on the precursor with the layered dense wall component composition and by generating different crystal sizes in a given layer by controlling crystallization process conditions, a porous hollow fiber membrane is formed, wherein each layer within the wall exhibits different pore sizes and different surface characteristics simultaneously. Furthermore, each layer, (hydrophilic or hydrophobic), can exhibit an asymmetric pore structure with smaller size pores adjacent to the exterior wall surface. Thus, alternating adjacent layers with different pore sizes and tailored hydrophobic and hydrophilic surface characteristics are formed.

It was found surprisingly that stable supported liquid membranes, SLMs, can be formed utilizing poly (aryl ether ketone) membranes. Poly (aryl ether ketone) membranes with homogeneous, asymmetric or multi-layer composite pore structures are utilized to form SLMs and to carry liquid-liquid extraction processes with these membranes. Poly (aryl ether ketone) membranes with multi-layer composite pore structures are particularly preferred.

In one preferred embodiment, the poly (aryl ether ketone) membrane with a layered porous wall structure is used to form supported liquid membranes. Preferably, the PAEK membrane is in the form of a hollow fiber, but the invention is not limited to this configuration. The wall of the porous poly (aryl ether ketone) membrane used for the preparation of SLMs consists of three distinct adjacent porous layers with alternating hydrophilic, hydrophobic, and hydrophilic characteristics. To form this layered structure, the dense wall of the precursor is etched to a predetermined depth from both sides of the article (in the case of hollow fibers from the exterior and the lumen side simultaneously) while maintaining the center dense region of the wall intact; the wall is etched from both sides to a predetermined depth leaving the central dense section intact; the thus formed porous sections of the wall formed by the etching process are functionalized with hydrophilic groups; the article is subjected to a further etching step to form a porous structure in the previously unaffected dense section in the center of the wall; the second etching step is carried out under conditions that preclude modification of the porous wall with hydrophilic groups. By controlling the etching process conditions during the initial etching step (the temperature and the etching reagent concentration), as well as the duration of the etching step, the initial porous layers of the desired thicknesses are formed. The thickness of the central substantially hydrophobic layer sandwiched between the two porous hydrophilic layers in the membrane wall is thus predetermined by the thicknesses of external porous layers. Thus, a layered porous wall structure is formed with interconnected hydrophilic, hydrophobic, and hydrophilic segments of predetermined thicknesses. The supported liquid membrane in the form of organic solution is encapsulated in the hydrophobic section of the membrane wall. The water-based feed and stripping solutions wet out the hydrophilic layers on the opposite sides of the membrane wall. The feed and stripping solutions form an intimate contact with the organic SLM layer to provide for a continuous solute transfer path from the feed to the stripping liquid.

More specifically, the hollow fiber membrane with three alternating adjacent hydrophilic, hydrophobic, and hydrophilic layers is prepared by a method comprising: (a) forming a blend of poly(aryl ether ketone) type polymer with a polyimide; (b) forming a shaped micro-capillary from the blend by extrusion; (c) crystallizing the poly (aryl ether ketone) phase in the shaped article; (d) bringing both side of the micro-capillary (external or internal) into contact with a primary amine for a predetermined period of time to affect decomposition of the polyimide in the exposed wall to a predetermined depth, while maintaining the central section of the wall thickness intact; (e) removing the low molecular weight fragments from etched wall segments; (f) functionalizing the thus formed porous segments of the wall with hydrophilic groups; (g) bringing the micro-capillary into contact with a primary amine to affect decomposition of the polyimide in the remaining dense central section of the wall; and (h) removing the low molecular weight fragments from the etched porous wall segment. The decomposition of the polyimide into low molecular weight fragments during steps (d) and (g) is carried out under conditions that do not cause functionalization of the membrane surface with the primary amine. Advantageously, the membrane is washed and dried following each etching step. The thus formed porous hollow fiber membranes are incorporated into a fluid separation device. In some embodiments, steps (d) through (h) are carried out in-situ in the preformed fluid separation device comprised of micro-capillaries.

The porous membranes of this invention separate components of fluid mixtures by selective permeation into extracting liquid. At least one solute from the liquid feed solution is transferred to the liquid extractant through the porous hollow fiber membrane, the feed solution and the extractant being substantially immiscible when in direct contact with each other, one of the solutions (the feed or the extractant) tends to preferentially wet the surface of the porous membrane to constitute a membrane-wetting liquid. The method comprises the steps of:
(a) contacting the first side of the porous hollow fiber membrane with the feed solution containing at least one solute;
(b) contacting the second side of the porous hollow fiber membrane with the liquid extractant so that the feed solution and the extractant can come into contact through the pores of the membrane; and
(c) removing the feed solution depleted of at least one solute from the feed side of said membrane while removing the extractant liquid enriched with at least one solute from the second side of said membrane, wherein the porous hollow fiber membrane is formed from a poly (aryl ether ketone) polymer.

The porous membranes of this invention form supported liquid membranes that separate components of a fluid mixture by selective permeation into an extracting liquid. At least one solute from the liquid feed solution is transferred to the liquid extractant through the porous hollow fiber membrane impregnated with an organic liquid, the feed solution and the extractant being substantially immiscible when in direct contact with the organic liquid. The organic liquid preferentially wets the surface of the porous membrane to constitute an immobilized membrane. The method comprises the steps of:
(a) contacting the first side of the porous hollow fiber membrane with the feed solution containing at least one solute said membrane impregnated with an organic liquid;

(b) contacting the second side of the porous hollow fiber membrane with a liquid extractant so that the feed solution and the extractant can come into contact through the organic liquid contained in pores of the membrane; and
(c) removing the feed solution depleted of at least one solute from the feed side of said membrane while removing the extractant liquid enriched with at least one solute from the second side of the membrane, wherein the porous hollow fiber membrane is formed from a poly (aryl ether ketone) polymer.

The porous PAEK hollow membranes of this invention can address a broad range of molecular transfers between phases, such as liquid-liquid extraction applications, including separation and recovery of pharmaceutical ingredients, peptides, amino acids, enzymes, biofuels, and metal ions.

The above and other features of the invention, including various novel details of construction and combinations of parts, and other advantages, will now be more particularly described with reference to the accompanying drawings and pointed out in the claims. It will be understood that the particular method and devices embodying the invention are shown by way of illustration and not as a limitation of the invention. The principles and features of this invention may be employed in various and numerous embodiments without departing from the scope of the invention.

BRIEF DESCRIPTION OF THE DRAWINGS

FIG. 2A shows a principal scheme of a liquid-liquid extraction process using porous poly (aryl ether ketone) hollow fibers formed into a cartridge, wherein the feed liquid containing a solute is introduced on the shell side of hollow fibers and the extractant liquid is introduced on the bore side of hollow fibers in a counter-current flow configuration. FIG. 2B is a cut-away view, taken along line B-B of FIG. 2A, showing the hollow fibers of the cartridge.

DETAILED DESCRIPTION OF THE PREFERRED EMBODIMENTS

Figure 1A:
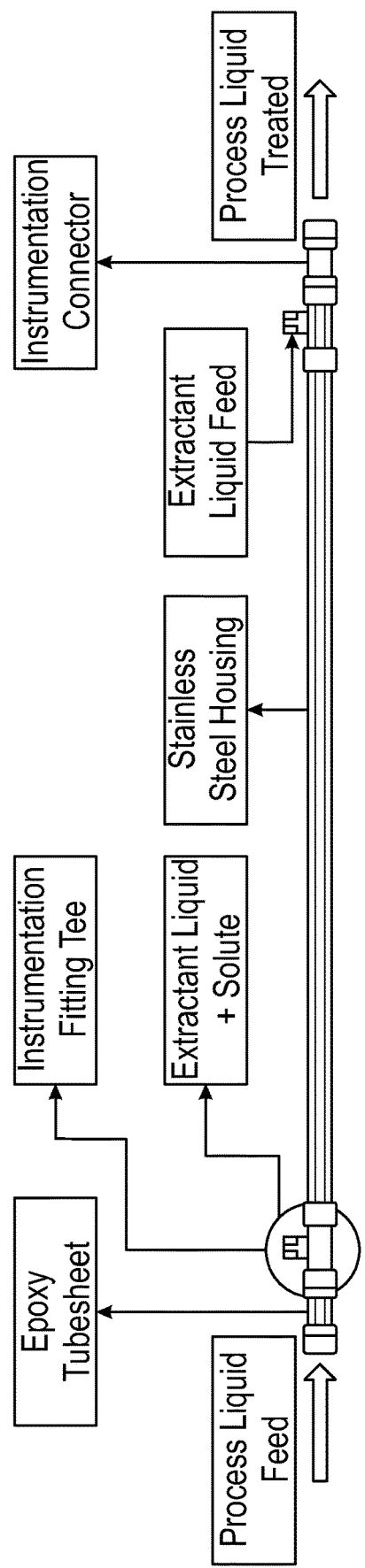
FIG. 1A shows a hollow fiber assembly used to conduct liquid-liquid extractions with PEEK hollow fibers, wherein the feed liquid containing a solute is introduced on the bore side of hollow fibers and the extractant liquid is introduced on the shell side of hollow fibers in a counter-current flow configuration.

Disclosed is the preparation of porous poly (aryl ether ketone), PAEK, hollow fiber membranes, and their use for a broad range of processes that involve the transfer of molecules between distinct phases. The present invention further provides novel methods for the transfer of molecules between phases and the removal and separation of target molecules from process streams employing porous PAEK hollow fiber membranes. The hollow fiber membranes are fabricated from poly (aryl ether ketone) polymers. A number of possible modes of molecular transfer between gas-liquid and liquid phases are possible according to the invention. In preferred embodiments, the PAEK hollow fibers are used to introduce reactant molecules into a reaction media and remove reaction products from a reaction media. The hollow fiber membranes are porous and exhibit mesoporous pore size. A mesoporous material is a material containing pores with diameters between 2 and 50 nm, according to IUPAC nomenclature. For comparison, IUPAC defines microporous material as a material having pores smaller than 2 nm in diameter and macroporous material as a material having pores larger than 50 nm in diameter.

The PAEK hollow fibers used in the processes of this invention preferably exhibit a nanoporous surface pore structure with a narrow pore size distribution and an average surface pore size between 5 and 100 nanometers, which is defined as mesoporous. Preferably, hollow fibers exhibit an asymmetric pore structure, wherein the surface pore size is between 5 and 100 nm, most preferably between 10 and 50 nm, and the interior pore size is larger than the surface pore size by a factor of two or more. The membrane is shaped as a hollow fiber (small diameter micro-capillary). In some embodiments, the interior porous structure of the hollow fiber may exhibit a bimodal pore size distribution. The bimodal distribution consists of a mesoporous pore fraction with an average pore size below 50 nanometer and a macro-porous pore fraction with an average pore size above 0.5 micron. It is further within the scope of this invention to utilize PAEK hollow fibers with a layered wall pore structure wherein individual layers differ in pore size. The layers are alternately nanoporous and macroporous. The porous hollow fiber surface characteristics are tailored towards application needs and can be hydrophobic or hydrophilic. It is further advantageous to utilize porous hollow fibers with Janus like pore characteristics wherein the membrane consists of a layered pore structure with alternating hydrophilic and hydrophobic surface properties.

The porous hollow fiber membranes of this invention are comprised of a poly (aryl ether ketone) or a blend of poly (aryl ether ketone)s. The preferred poly (aryl ether ketone)s are poly (ether ether ketone), PEEK, poly (ether ketone), PEK, poly (ether ketone ketone), PEKK, and poly (ether ketone ether ketone ketone), PEKEKK, as well as their copolymers. The poly (aryl ether ketone)s are manufactured by Victrex Corporation under the trade names Victrex® PEEK, Victrex® PEEK HT, and Victrex® PEEK ST. Poly (ether ether ketone) is further available from Solvay under trade name KetaSpire™ and another poly (aryl ether ketone) is available from Solvay under the trade name AvaSpire®. Poly (ether ether ketone) is further available from Evonik under the trade name VESTAKEEP®.

The porous PAEK hollow fibers of this invention are semi-crystalline. Namely, a fraction of the poly (aryl ether ketone) polymer phase is crystalline. A high degree of crystallinity is preferred, since it imparts solvent resistance and improves the thermo-mechanical characteristics of the hollow fiber. In some embodiments of this invention, the degree of crystallinity is at least 10%, preferably at least 25%, and most preferably at least 30%.

The preferred method of forming the porous PAEK hollow fibers is by melt processing. The preparation of the porous poly (aryl ether ketone) hollow fiber typically consists of the following steps: (1) Forming a blend of poly (aryl ether ketone) polymer with a pore-forming material (porogen) by melt blending—the porogen is alternatively a diluent (a high boiling, low molecular weight liquid or solid), an intermediate molecular weight oligomer, a polymer or a mixture thereof; (2) Forming a shaped hollow fiber from the blend by melt processing, such as an extrusion process; (3) Solidifying the shaped hollow fiber by cooling; (4) Optionally, annealing the shaped article to increase the degree of crystallinity; (5) Removing the porogen (the porogen is typically removed by extraction); and (6) Drying the porous hollow fiber comprised of PAEK polymer.

Hollow fibers produced by high-speed melt processing undergo rapid cooling and can be substantially amorphous. Prior to or subsequent to pore-forming material removal from the hollow fiber, the hollow fiber is treated to increase the degree of crystallinity of the PAEK phase. The crystallization can be induced by a thermal process, via solvent-induced crystallization, or by a combination of solvent-induced crystallization followed by a thermal treatment. Both methods are known in the art. The term annealing as defined herein refers to a processing step or condition that leads to an increase in the degree of crystallinity of the PAEK phase. The annealing can take place during the solidification step through control of the cooling rate. For example, the annealing can be carried out in line during the extrusion step by controlling the cooling rate. Alternatively, or in an addition, the annealing can be carried out in a subsequent step after the hollow fiber has been formed by solidification. In the latter case, the solidified hollow fiber can be placed in an oven or transported through a heating zone for a period of time sufficient to effect crystallization. The article can be annealed at a temperature from about 150° C. to about 330° C., preferably from about 200° C. to about 310° C., most preferably from 250° C. to about 310° C., to increase the crystallinity of the PAEK phase prior to the removal of the porogen. Solvent-induced crystallization can be carried out utilizing solvents known to induce polymer crystallization, such as tetrahydrofuran, chlorinated solvents, such as methylene chloride, 1,3-dichloropropane, chlorobenzene, high boiling alcohols or ethers or ketones, such as methyl ethyl ketone, acetone, and cyclopentanone. The solvent treatment can be carried out at an elevated temperature, but preferably below the boiling point of the solvent. Craze cracking is known to accompany solvent-induced crystallization and must be avoided. The annealing can take the form of a combination of the thermal and solvent treatment steps to affect the optimal degree of crystallization and morphology. The annealing protocol is known to affect crystalline structure which, in turn, affects pore structure. The PAEK/porogen weight ratio in the blend can range from 20/80 to 60/40 and following porogen removal produce hollow fibers with pore volume between 40 and 80%.

Pore-forming additives can include high boiling solvents, compatible oligomers, nanoparticles, or compatible or semi-compatible polymers. The use of compatible polymers or their mixtures with partially compatible polymers or nanoparticles as porogens is generally preferred. Preferred polymeric porogens include melt-processable polyimides and their mixtures with polysulfones, such as poly (ether sulfone) and poly (ether ether sulfone). The nanoparticles are soluble organic or inorganic materials. Inorganic nanoparticles, such as sodium chloride and sodium carbonate, are preferred. The most preferred polymeric pore-forming additives are aromatic polyimides. Poly (aryl ether ketone) type polymers form compatible blends with certain aromatic polyimides, PI. Removal of the polyimide component from such blend articles by solvent extraction, however, can be difficult due to polymer chain entanglement. The polyimide can be quantitatively removed by selective chemical decomposition of the polyimide phase to form the final porous article. This method of porous PAEK material preparation is referred to as the reactive porogen removal process, RPR.

Polyimides that form a compatible precursor blend with poly (aryl ether ketone) polymers are defined as polymers containing

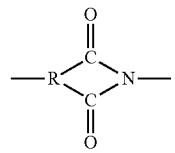

linkages and include aliphatic and aromatic polyimides, copolyimides and polyimide block and graft copolymers, wherein the polyimide is defined as a molecule that contains at least two imide linkages. Additional polyimides include aromatic polyamide imides, polyhydrazine imides and polyester imides.

Aromatic polyimides are particularly useful for the preparation of porous hollow fibers of this invention. The most preferred polyimide is poly (ether imide), PEI, of the following formula:

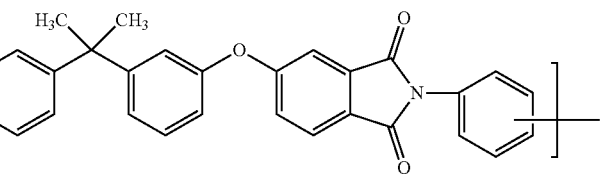

and poly (ether imide) copolymers manufactured by the Sabic Industries under trade names Ultem® 1000, Ultem® XH1010F, Ultem® 6050 and Siltem® STM1500. The copolymers that contain dimethylsiloxane or sulfone units are examples of representative copolymers. Another preferred polyimide is Aurum® manufactured by Mitsui and distributed by DuPont Engineering Polymers.

The polyimides can be used as a single additive component or as a mixture of polyimides. The polyimides typically have an average molecular weight in the range of 500 to 1,000,000 Daltons, preferably between 1,000 to 500,000 Daltons.

Mixtures of poly (ether imide) with poly (ether sulfone), PES, poly (ether ether sulfone), PEES, or polycaprolactone are also within the scope of this invention. The additional pore-forming components supplement the PEI pore-forming material and augment pore structures formed from two-component PAEK/PEI blends. These supplemental additives are considered compatible PEI components. PAEK hollow fibers prepared from blends containing multiple pore-forming components exhibit bimodal pore distributions that combine mesopores below 50 nanometer size with macropores above 0.1 micron size. The PAEK substrate with this combination of pore sizes can increase the rate of solute transfer. The PAEK polymer concentrations in blends containing multiple pore-forming components range from 20 to 60 percent by weight, while PEI/supplemental compatible component weight ratios in the multi component blends range from 20/80 to 80/20.

The formation of the binary poly (aryl ether ketone) blend with the polyimide or multicomponent blends can be carried out by mixing components in a molten stage, such as by melt compounding, and other methods conventionally employed in the polymer compounding industry. The use of a twin extruder is the preferred method of blending. A plasticizer can be optionally added to aid processing. The poly (aryl ether ketone)/polyimide blends form compatible blend compositions. The compatible blend typically exhibits a single glass transition temperature. The compatible composition is defined as capable of forming nanoporous poly (aryl ether ketone) articles with interconnected pore structure and a major fraction of pore volume having a pore diameter in the range of 5 to 100 nanometers. Preferred blends are PEEK/PEI, PEK/PEI and PEKK/PEI blends that form poly (aryl ether ketone) hollow fibers with interconnected pore structure. The multicomponent PAEK/PEI/compatible blends that form poly (aryl ether ketone) hollow fibers with interconnected pore structure and bimodal pore distribution with a combination of meso and macro pores are also preferred. The specific molecular transfer process conditions determine the desired pore size and pore size distribution that, in turn, is determined by PAEK and polyimide selection, by PAEK/PEI ratio and crystallization protocol. Incorporation of supplementary PEI competitive additives into blend compositions and downstream processing conditions, such as annealing temperature, further affect PAEK hollow fiber morphology and can be used to tailor porous structure.

Hollow fibers with graded pore structure consisting of a thin nanoporous surface layer supported by a macroporous bulk wall structure exhibit higher solute mass transfer rates while maintaining good stability. Hollow fibers with a layered graded pore structure are formed by coextrusion processes from membrane forming compositions with different contents of pore-forming materials. It is also within the scope of the invention to utilize hollow fibers with an asymmetric wall pore structure wherein the mesoporous smaller pore size layer is located at both the external and the lumen side of the hollow fiber. Two or more poly (aryl ether ketone)/polyimide blends of different blend compositions can be formed in step (a) and coextruded in step (b) to form a micro-capillary with a variable layered wall composition. Upon polyimide phase extraction the capillary formed by coextrusion will have a different pore size in each layer. The crystallization protocol in step (c) affects PAEK crystal size which, in turn, affects the pore size of the wall layer upon removal of the polyimide phase. Thus, the porous wall structure in these embodiments can be homogeneous, asymmetric, or multi-layer composite. The surface functionality of hollow fibers that have been fabricated with the predetermined homogeneous, asymmetric or multi-layer composite pore structure can be uniform throughout the wall cross-section and selected between the hydrophilic or the hydrophobic options, respectively. Alternatively, individual layers in multi-layer hollow fibers can carry different surface functionality.

In some embodiments of the present invention, the poly (aryl ether ketone) hollow fiber membranes with a layered porous wall structure, wherein each layer carries a different surface functionality, are used to carry out liquid-liquid extraction processes. The wall of the Janus-like porous poly (aryl ether ketone) hollow fiber membrane is formed with alternating hydrophilic and hydrophobic layers. To form the layered structure, the dense wall of the precursor dense hollow fiber is etched to a predetermined depth from one side only, while maintaining the adjacent dense region intact; the thus formed porous section of the wall formed by the etching process is functionalized with hydrophilic groups; the article is subjected to further etching to form a porous structure in the previously unaffected dense section; the second etching step is carried out under conditions that preclude modification of the porous wall with hydrophilic groups. By controlling the etching process conditions during the initial etching step (the temperature and the etching reagent concentration), as well as the duration of the etching step, the initial porous layer of desired thickness is formed. The thickness of the second layer in the membrane wall is thus predetermined by the thickness of the initial porous layer. Thus, a layered porous wall structure is formed with interconnected hydrophilic and hydrophobic segments of predetermined thicknesses. The water-based liquid tends to wet-out the hydrophilic porous layer, while the organic liquid tends to wet-out the hydrophobic porous layer. The feed solution and the extractant thus come into contact through the hydrophilic and the hydrophobic layer within the porous wall of the membrane enabling an efficient solute transfer.

The poly (aryl ether ketone)/porogen blends are fabricated into hollow fibers by melt extrusion. The hollow fiber preferably possesses an outside diameter from about 50 to about 2000 micrometers, more preferably from about 80 to about 1000 micrometers, with a wall thickness from about 10 to about 100 micrometers. Prior to porogen phase removal, the hollow fiber is preferably annealed to increase the degree of crystallinity of the PAEK phase. As discussed above, the annealing can take place during the solidification step through control of the cooling rate, by a subsequent thermal treatment or by other methods known in the art such as a solvent treatment to induce crystallization. The preferred porogen is an aromatic polyimide.

The removal of the polyimide component from the preformed hollow fiber can be effectively carried out by the RPR process utilizing reagents that decompose the polyimide into low molecular weight easily extractable fragments. The suitable classes of reagents include, but are not limited to, strong inorganic bases, ammonia, tetraalkylammonium hydroxides, hydrazine, alkylhydrazines, hydroxyalkylhydrazine, primary aliphatic amines, or secondary aliphatic amines. In some embodiments, the reagent that affects polyimide decomposition is diluted with a solvent and/or contains water. Examples of suitable solvents include alcohols, ketones, hydrocarbons, water, and aprotic solvents such as NMP, DMF, and the like. Amine reagents suitable to decompose the polyimide phase in accordance with this invention include, but are not limited to, primary and secondary amines, such as methylamine, ethylamine, propylamine, butylamine, ethylenediamine, propylenediamine, butylenediamine, morpholine, piperazine, monoethanolamine, ethylethanolamine, diethanolamine, propanolamine, dipropanolamine, and mixtures thereof. Commercially available amine mixtures, such as Ucarsol®, can be also employed. The preferred amines include hydrazine, monoethanolamine, tetramethylammonium hydroxide, and their mixtures with alcohols, such as methanol, ethanol, isopropanol, or butanol, ketones, water, and aprotic solvents. The most preferred reagents for the decomposition of the polyimide phase are inorganic bases, the monoethanolamine, MEA, hydrazine and the tetramethylammonium hydroxide.

The decomposition and removal of the polyimide component can be carried out at an ambient temperature, but preferably is carried out at elevated temperatures to facilitate the decomposition process and the removal of decomposition products. Preferably, the polyimide decomposition process and the removal of the low molecular weight decomposition product are carried out concurrently in a common solvent media. The comprehensive removal of decomposition products may require additional washing. In one embodiment of this invention, the polyimide decomposition and removal process is carried out in a neat MEA solvent at temperature from about 50° C. to about 180° C., preferably from about 80° C. to 150° C. The time required to fully decompose polyimide and to remove products of the decomposition process from the hollow fiber will depend on the fiber dimensions and crystalline morphology, the amount of PEI fraction and the thickness of the hollow fiber wall, as well as process conditions, including reagent concentration, agitation rate, temperature and the like, as will be recognized by those skilled in the art. The thus formed porous poly (aryl ether ketone) hollow fiber is then washed with an alcohol, water, or other suitable solvent and dried.

In one embodiment, the preparation of porous PAEK hollow fiber and its surface modification is carried out simultaneously in a single-step process. Namely, if the porous PAEK hollow fiber is formed by the RPR process from the PAEK/PEI blend utilizing a primary amine as the polyetherimide removal reagent, the reaction can be carried out under conditions that affect both the formation of the porous PAEK hollow fiber and the modification of the porous hollow fiber surface via attachment of primary amine molecules via ketimine group formation in a single-step process. The primary amine of a general formula $H_2N$—R—X can be utilized to affect RPR process and surface functionalization wherein X is a hydrophilic functional group, such as an —OH group. Carrying out the RPR process at elevated temperatures, preferably above 80° C., most preferably from about 100° C. to about 120° C., in an anhydrous reaction media while utilizing a high concentration of amine reagent, leads to the formation of a porous and functionally modified PAEK hollow fiber in a single step. In one such example, porous PEEK hollow fiber modified with ≈C═N—$CH_2CH_2OH$ groups is formed in a single step process from PEEK/PEI blend by reacting the precursor blend hollow fiber with the neat monoethanolamine at about 120° C. In another example, the porous PEEK hollow fiber is formed while simultaneously functionalized by the reaction with diethylenetriamine. The surface of porous PAEK hollow fiber is thus functionalized with ≈C═N—$CH_2CH_2$—NH—$CH_2CH_2$—$NH_2$ groups. The Schiff base ketimine group can be hydrolytically unstable. The imine group can be converted to a stable secondary amine group by reduction. Thus, a mesoporous PAEK hollow fiber with hydrophilic surface characteristics is formed.

In some embodiments, it is desirable to form the porous PAEK hollow fiber without hydrophilic surface modification to maintain the hydrophobic surface characteristics. The mesoporous PAEK hollow fiber surfaces of unmodified hollow fiber are substantially hydrophobic and not easily wetted with water but are wetted with organic liquids. To form an unmodified porous PAEK article by the RPR process, the precursor PAEK/PEI blend hollow fiber is contacted with a strong organic or inorganic base to decompose and remove PEI pore-forming phase. If a primary amine is used to remove PEI phase, the reaction is carried out under conditions that suppress ketimine group formation, i.e., the reaction is carried out at moderate temperatures and in a relatively dilute amine solution that preferably further contains water. It will be recognized by those skilled in the art that, by selecting balanced reaction conditions, the modification of PAEK hollow fiber surface via the formation of imine linkages can be largely suppressed, while an adequately high rate of PEI phase decomposition and removal is still maintained. For example, the RPR process can be carried out utilizing a monoethanolamine/dimethylformamide/water mixture 20/70/10 by volume at 80° C., which provides for a porous PAEK hollow fiber formation while suppressing surface functionalization via the ketimine group formation. The preferred reaction temperature utilizing the monoethanolamine/dimethylformamide/water mixtures is from about 70° C. to about 100° C. The unmodified mesoporous PAEK hollow fiber can be modified with target hydrophilic functional groups in a subsequent step.

The nanoporous PAEK hollow fibers of this invention can have a uniform pore size and pore size distribution across the entire hollow fiber wall thickness. However, in preferred embodiments, it is advantageous to structure the hollow fiber wall as a layered structure with distinct regions of variable average pore size and/or pore volume. It is advantageous to form hollow fiber membranes utilizing a porous wall with an asymmetric pore structure to increase the solute transfer rate. One method of forming high solute transfer rate PAEK hollow fibers of this invention is by forming a multi-layer porous wall structure with a smaller size nanopore exterior layer and a larger pore size macro-porous interior wall layer. Multi-layer hollow fibers of this invention are formed by co-extruding PAEK/pore-forming additive blend compositions that differ in pore-forming additives composition and/or additive weight fraction. The method provides for the preparation of hollow fibers with 2 to 10, preferably 2 to 4, distinct porous wall layers of variable average pore size. In one embodiment, the hollow fiber porous wall structure consists of two layers with the exterior layer exhibiting an average pore diameter below 50 nanometers, preferably between 10 and 30 nanometers, and the interior wall layer exhibiting an average pore diameter above 0.1 micron. In another embodiment, the hollow fiber porous wall structure is comprised of three layers with the interior layer exhibiting an average pore diameter below 50 nanometers, preferably between 10 and 30 nanometers, sandwiched between two exterior wall layers exhibiting an average pore diameter above 100 nm, most preferably above 1 micron. This three-layer structure is particularly useful for the preparation of supported liquid membranes (SLM).

In one example, a hollow fiber with a multilayer wall structure is formed by coextrusion of two PEEK/PEI blends of the different blend compositions. After PEI pore-forming material is removed, a porous wall with two layers of distinct pore size and pore volume is formed. The asymmetric pore structure provides for reduced resistance to solute transfer. It is also within the scope of the present invention to form multilayer hollow fiber with multiple zones that differ in pore size. The multi-zone porous hollow fiber that contains porous zones that differ by at least about 10% in the average pore size or by at least about 5% in the pore volume impart certain advantages to mechanical or functional characteristics to the hollow fiber. For example, the multi-zone porous hollow fiber can provide improved mechanical properties while increasing solute transfer rate. The multi-zone porous hollow fiber formed from two or more PEEK/porogen blends can contain different PEEK porogen components or differ in the PEEK/porogen ratio. The PEEK polymer content of the first blend can differ from the PEEK polymer content of the second blend and any additional blends by between 5 to 50 weight percent, preferably by at least 10 to 25 weight percent. The blend composition of individual layers can further differ in the PAEK polymer composition. For example, PEEK can be used as the wall forming material in one layer while PEK or PEKK can be used as the wall forming material in an adjacent layer.

The multilayer hollow fiber of the desired dimensions and configuration can contain two, three, or more contiguous layers that differ in the average pore size and/or pore volume. Furthermore, the individual layer can vary from about 5% of the overall hollow fiber wall thickness to 50% of the overall wall thickness. The thickness of each layer can be controlled and can be as thin as 10 micrometers or less.

The semi-crystalline mesoporous PAEK hollow fibers are highly solvent and temperature resistant. This enables modification of pore surfaces without affecting preformed pore structure when surface hydrophilization or further surface hydrophilization are required. The semi-crystalline morphology imparts solvent resistance and enables the use of a broad range of organic solvents for the liquid-liquid extraction processes of the present invention. The surface functional groups are selected to impart target hydrophilic or hydrophobic characteristics to individual porous layers. It is within the scope of the instant invention to functionalize a predetermined layer in the multilayer hollow fiber wall structure only. For example, only one layer in the two-layer hollow fiber is functionalized with hydrophilic functional groups while the second unfunctionalized layer remains substantially hydrophobic. The hydrophilic layer will wet out with a water-based solution and the hydrophobic layer with the organic solvent solution during the liquid-liquid extraction process. The solute transfer between the two phases thus takes place within the wall of the hollow fiber. Individual layers in a three-layer hollow fiber can be functionalized separately or sequentially. Both exterior layers in the three-layer wall structure can be functionalized with hydrophilic functional groups, while the middle layer sandwiched between the exterior layers is left unfunctionalized and substantially hydrophobic. Thus, the functionalized three-layer structure is particularly useful for the preparation of supported liquid membranes (SLM). The organic solvent containing active carrier is contained in the middle hydrophobic layer, while water-based feed solution and extractant liquid wet out the exterior hydrophilic wall layer. The selective solute transfer between the feed solution and the extractant takes place via SLM contained in the hydrophobic layer. The three-layer configuration increases the stability of the SLM layer.

To form the three-layered structure with different surface functionality in individual layers, the dense wall of the precursor is etched to a predetermined depth from both sides of the article (in case of hollow fibers, from the exterior and the lumen side simultaneously) while maintaining the center dense region of the wall intact; the wall is etched from both sides to a predetermined depth leaving the central dense section intact; the thus formed porous sections of the wall formed by the etching process are functionalized with hydrophilic groups; the article is subjected to a further etching step to form a porous structure in the previously unaffected dense section in the center of the wall; and the second etching step is carried out under conditions that preclude modification of the porous wall with hydrophilic groups. The interior wall section is substantially hydrophobic. The functionalization of the PAEK hollow fiber membrane surface with hydrophilic groups is described in the following sections. By controlling etching process conditions during the initial etching step (the temperature and the etching reagent concentration) as well as the duration of the etching step, the initial porous layers of the desired thicknesses are formed. The thickness of the central substantially hydrophobic layer sandwiched between the two porous hydrophilic layers in the membrane wall is thus predetermined by the thicknesses of the initial porous layers. Thus, a layered porous wall structure is formed with interconnected hydrophilic, hydrophobic, and hydrophilic segments of predetermined thicknesses. The supported liquid membrane in the form of organic solution is encapsulated in the hydrophobic section of the membrane wall. The water-based feed and stripping solutions wet out the hydrophilic layers on the opposite sides of the membrane wall. The feed and stripping solutions form an intimate contact with the organic SLM layer to provide for a continuous solute transfer path from the feed solution to the stripping liquid.

Initial functionalization of porous PAEK hollow fibers by functional groups to impart hydrophilic surface characteristics may include, ethylene oxide groups, carboxylic groups, hydroxyl groups, primary, secondary or tertiary amino groups, quaternary amino groups, or sulfonic acid groups to name a few. In some embodiments, the functional groups on the PAEK porous hollow fiber surface are formed by a direct chemical reaction. For example, the unmodified porous PAEK hollow fibers prepared as described above can be modified by reducing surface ketone groups to form hydroxyl groups or by reacting ketone groups with multifunctional primary amine reagents via ketimine group formation to impart the target hydroxyl or amine group functionality. The surface functionalization is carried out without affecting crystalline regions of the PAEK polymer phase to preserve the solvent chemical resistance of the functionalized hollow fibers. The concentration of chemical groups in functionalized layers is preferably above 0.1 mmol/g, most preferably above 0.5 mmol/g.

The PAEK hollow fibers functionalized with hydroxyl, primary, secondary, tertiary or quaternary amino groups, carboxylic groups or sulfonic acid groups are particularly preferred for hydrophilic surface formation. The >C=O ketone group in the PAEK polymer backbone, in particular, can be used to form functional groups on the PAEK substrate's surface. The high concentration of ketone groups in poly (ether ether ketone), poly (ether ketone), and poly (ether ketone ketone) polymers provide for a high concentration of functional surface groups upon chemical modification.

The >C=O ketone group in the PAEK backbone can be reduced to a >C—OH hydroxyl group. The surface hydroxyl groups can be formed by reducing ketone groups on the surface of the PAEK hollow fiber with a reducing reagent, such as sodium borohydride. The surface hydroxyl groups can be further introduced by forming =C=N—CH$_2$—CH$_2$—OH functional groups on the PAEK surface via reaction with monoethanolamine. Direct reduction of ketone groups on the mesoporous surface of PAEK to form diphenylmethanol functional units,

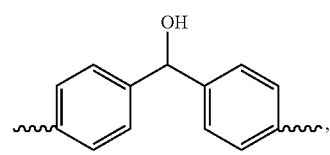

is particularly preferred. The formation of diphenylmethanol by selective reduction of ketone groups in PEEK polymer is further illustrated as follows:

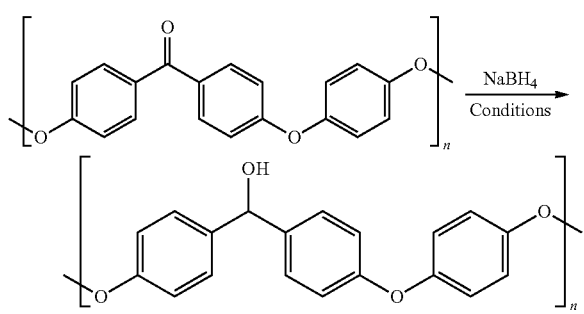

The reduction conditions are selected to modify pore surfaces in amorphous regions without affecting crystalline regions. The surface functionalization with —OH groups can be carried out on a preformed porous asymmetric PAEK hollow fiber or utilizing a non-porous shaped PAEK article containing pore-forming material followed by pore-forming material removal to form the final asymmetric surface-functionalized membrane. It is desirable to conduct surface functionalization without affecting crystalline phase. Loss of crystallinity during functionalization, including functionalization by —OH groups, can lead to a loss of preformed pore morphology. Loss of crystalline phase can further lead to the loss of solvent resistance. The functionalization via modification of ketone groups is best carried out under reaction conditions that minimize chemical alteration of the crystalline phase.

A number of reducing agents known in the art can be utilized, including $NaAlH_4$ and $NaBH_4$. The use of mild reducing agents, such as $NaBH_4$, is preferred to preserve the crystalline structure and pore morphology in preformed asymmetric PAEK hollow fibers. The use of mild reaction conditions, such as the use of less aggressive solvents and modest reaction temperatures, is further preferred. In some embodiments, the surface functionalization of non-porous preformed PAEK articles can be carried out under more aggressive conditions, since the underlying pore morphology is formed following functionalization. The preferred method of ketone group reduction is the use of $NaBH_4$ reagent in isopropyl alcohol, IPA, solution or tetrahydrofuran, THF, solution that further contains polyethylene glycol, PEG, such as PEG 500. It was found surprisingly that the addition of PEG provides for improved reaction conditions and consumption of the reducing reagent.

The degree of substituting by functional groups can be controlled via reagent concentration, reaction conditions (in particular temperature), and reaction duration. The formation of functional groups can be followed by AT-FTIR spectroscopy, XPS spectroscopy or other methods known in the art. In the spectra of PAEK polymers there are two peaks associated with the carbonyl group; a main feature is the carbonyl asymmetric stretching peak at around 1644 $cm^{-1}$, and the skeletal vibration at 1651 $cm^{-1}$ in PEEK and 1655 $cm^{-1}$ in PEK. The skeletal in-plane vibration of the phenyl rings at 1498 $cm^{-1}$ is present in all PAEK polymers. Following surface reduction, the concentration of ketone groups is reduced and is reflected by the reduction in the intensity of the peak at 1644 $cm^{-1}$. The change in the ratio of the 1644 $cm^{-1}$ peak as related to the phenyl rings at 1498 $cm^{-1}$ can be used to follow the progress of ketone group reduction. The reduction of the ketone group is accompanied by the appearance of —OH stretching vibration in AT-FTIR spectra.

However, a quantitative determination of functional group concentration by surface measurement methods can be difficult. The concentration of —OH groups in PAEK-OH materials can be measured quantitatively by UV-VIS spectroscopy as follows: the PAEK-OH materials form a distinct red color upon dissolution in concentrated sulfuric acid. Sulfuric acid is essentially the only solvent capable of dissolving semi-crystalline PAEK materials at room temperature. The color of PAEK-OH solutions is distinctly different from the color of the unmodified material dissolved in sulfuric acid. The model compound MBPPM—bis(4-(4-methoxyphenoxy)phenyl)methanol dissolved in sulfuric acid was used to construct a calibration curve that was used, in turn, to measure the concentration of —OH groups in functionalized PAEK materials. The solution of MBPPM in sulfuric acid was used to construct a calibration curve using the absorption peak at 508 nm. The calibration curve was used to measure concentration of —OH groups in mesoporous PAEK membranes functionalized under different protocols.

The UV-VIS method of measuring hydroxyl group concentration is highly sensitive and allows determination of the concentration of —OH groups in surface functionalized PEEK-OH materials. The method enables the optimization of reaction conditions to control the degree of surface functionalization and the depth of the functionalized surface layer. The concentration of functional groups can be measured as a function of time and represented as a weight concentration (mmol/g units) or as a surface group concentration (µmmol/$cm^2$ units). High concentration of surface groups can be attained in a short reaction duration time. The concentration of surface groups above $1\times10^{-5}$ µmol/$cm^2$ is preferred; most preferred is surface group concentration above $5\times10^{-5}$ µmol/$cm^2$.

The porous PAEK substrate functionalized with hydroxyl groups can be further converted to the desired new functionality through chemical transformations of —OH groups. For example, the surface of porous PAEK articles can be functionalized with carboxylic groups utilizing a common key-intermediate, a PAEK-OH functionalized material. The latter is obtained by surface reduction of ketone groups in benzophenone linkage. Substitution of hydroxyl groups, under mild acidic conditions, with 4-ammobenzoic acid and succinamic acid provides for PAEK-Ph-COOH and PAEK-$(CH_2)_2$—COOH functionality. The PAEK-OH functionalized material can be reacted with a sultone, for example 1,4-butane sultone, under basic conditions to form sulfonic acid functionalized surface.

A broad method of PAEK hollow fiber hydrophilization is via reaction of the ketone group in a PAEK backbone with a functional hydrocarbon containing a primary amino group. In this embodiment, the ketone groups in the poly (aryl ether ketone) backbone are reacted with a low molecular weight hydrocarbon, oligomer, or a polymer containing primary amino-functional groups ~$NH_2$. The attachment of the target molecule to the substrate is thus carried out utilizing the primary amino group and is completed via the ketimine group formation. Optionally, in some embodiments this reaction is followed by ketimine group reduction to form a durable covalent bond of molecules containing functional groups to the PAEK hollow fiber surface.

The functional hydrocarbon molecule is attached to the PAEK hollow fiber surface via formation of ketimine linkages as further illustrated below:

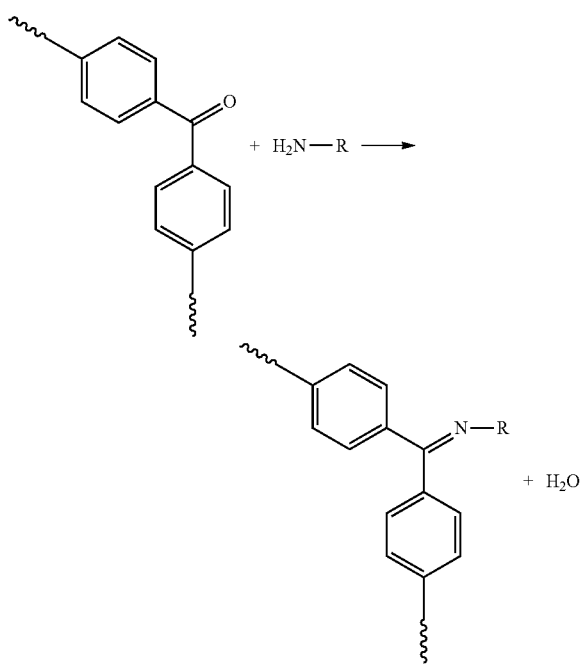

wherein R is a low molecular weight hydrocarbon, oligomer or a polymer containing primary amino-functional groups ~$NH_2$ and at least one additional functional group, such as a hydroxyl group, an amino group, or a carboxylic group, wherein R is an aliphatic or an aromatic radical. Difunctional and multifunctional amines are particularly preferred. Examples of difunctional amines include ethylenediamine, propylene diamine, iso-butylene diamine, 1,4-diaminobutane, diethylenetriamaine, ethylethanolamine, diaminocyclohexane, phenylenediamine, toluene diamine. In one example, R radical contains multiple amino groups to provide a PAEK surface with a high concentration of functional groups. Molecules containing a high concentration of primary amino groups are particularly preferred. Polyvinylamine or poly (ethylene glycol) diamine is utilized to form highly hydrophilic surfaces. Poly (ethylene glycol) diamine of the general formula

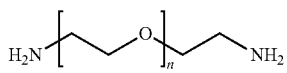

is such a dual functional R molecule. In preferred embodiments, n can range from 3 to 12.

In some embodiments, the $H_2N$—R molecule contains hydroxyl functional groups rather than an additional amino group. Primary amino hydrocarbons containing hydroxyl groups can be utilized to hydrophilize the PAEK surface. The tertiary or secondary alcohols, ≈C=N—R—OH, or primary alcohols, ≈C=N—R—$CH_2$—OH, are attached to the PAEK porous media via the Schiff base linkage formation (R is an aliphatic, an aromatic or heterocyclic hydrocarbon radical). In some embodiments, it is desirable to reduce the ketimine linkage to form a secondary amine forming ≈C—NH—R—OH or ≈CH—NH—R—$CH_2$—OH groups. The secondary amine group is a more hydrolytically stable bond. In some embodiments, the secondary amine group is further alkylated to form a tertiary amine.

The functionalization of the PAEK hollow fiber surface with ≈C=N—$CH_2CH_2OH$ groups can be carried out by reacting ketone groups in the PAEK backbone with monoethanolamine. This can be conveniently carried out during the RPR process, wherein the porous structure formation and functionalization take place simultaneously. Alternatively, the pre-formed nanoporous PAEK hollow fiber is reacted with the monoethanolamine in a separate step. Other aliphatic amino functional alcohols, such as diethanolamine, propanolamine, dipropanolamine, or 4-amino-1-butanol, can be utilized. One preferred $H_2N$—R—OH linker molecule is amino-functionalized poly (ethylene glycol). The $H_2N$—R—OH molecules containing aromatic rings are another class of functional groups that are used to functionalize the surface with hydrophilic groups.

Preparation of amino-functional surfaces via Schiff base linkage in some embodiments is followed by ketimine group reduction. In the first step, the porous PAEK hollow fiber is reacted with a multi-functional primary amine radical, such as difunctional hydrocarbon radical, $H_2N$—R—$NH_2$. In the second step, the ketimine group is reduced using $NaBH_3CN$, to form PEEK—NH—R—$NH_2$ functionalized surface.

The PAEK hollow fiber configuration is highly flexible and the hollow fibers can be packaged into a membrane device or a membrane module for the countercurrent liquid-liquid extraction processes of the present invention. The term "membrane module" as used herein refers to a plurality of PAEK hollow fibers formed into a bundle and incorporated into a membrane device having a first entrance port in communication with the feed fluid and a second exit port for the exit of the treated feed fluid depleted of the dissolved solute, a third entrance port for introduction of the extractant and a fourth exit port for the removal of the extractant fluid enriched in the solute. The hollow fibers are formed into a structured bundle or cartridge of a uniform length and packing density. All hollow fibers in the bundle preferably are of equal length. Hollow fibers in the membrane bundle differ in length by less than 10%, preferably by less than 5%, and most preferably by less than 1%. Forming structured bundles from small capillaries (also referred to as hollow fibers) is known in the art and includes weaving, computer-controlled helical winding, and forming processes. These methods are disclosed in U.S. Pat. Nos. 3,735,558; 3,755,034; 3,794,468; 4,207,192; 4,881,955: 5,026,479; 5,224,522; 5,263,982; 5,282,964; 5,598,874; 5,702,601; 5,837,033; and 7,264,725 One preferred method of forming a structured bundle of PAEK capillaries is by the use of computer-controlled helical winding.

The hollow fiber device transfers molecules from a first phase into a second phase without phase intermixing, such as the solute from the liquid feed solution to the liquid extractant through porous poly (aryl ether ketone) hollow fiber membranes. The feed solution and the extractant being substantially immiscible when in direct contact with each other, one of the solutions the feed or the extractant tends to preferentially wet the surface of the porous hollow fiber membrane and constitutes a membrane-wetting liquid. The hollow fiber membranes are sealed in a housing in a fluid-tight configuration wherein the housing is equipped with a first feed port for the introduction of liquid feed solution and a second port for the withdrawal of the feed solution, a third port for the introduction of the liquid extractant and a fourth port for withdrawal of the liquid extractant wherein at least a fraction of the solute is transferred from the feed solution to the liquid extractant.

Figure 2C:
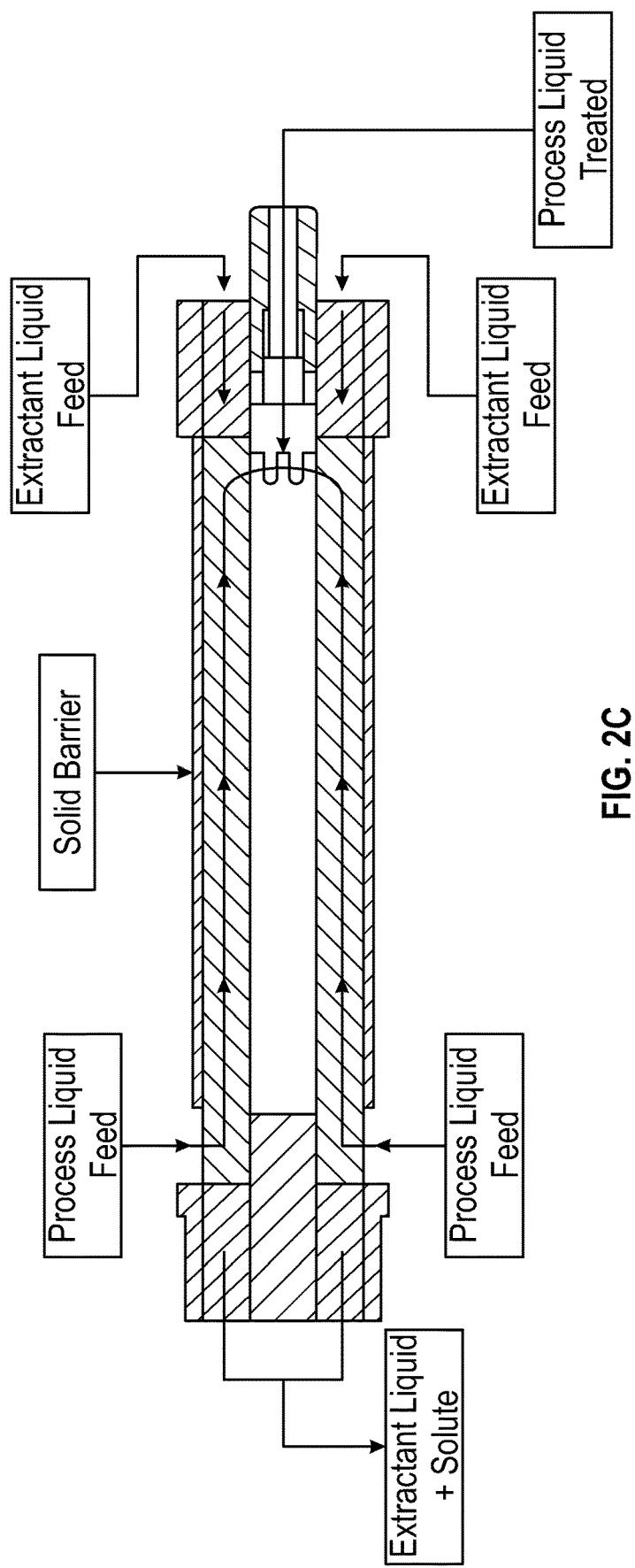
FIG. 2C is a partially cross-sectional view of the cartridge of FIG. 2A.

The principal scheme of the liquid-liquid extraction process using porous poly (aryl ether ketone) hollow fibers formed into a cartridge is depicted in FIGS. 2A-2C. The feed liquid containing a solute is introduced on the shell side of hollow fibers and the extractant liquid is introduced on the bore side of hollow fibers in a counter-current flow configuration. Target solute is transferred from the feed solution into the extractant liquid. The cartridge is constructed from a bundle of hollow fibers with terminal ends encapsulated into tubesheets. Tubesheet ends are severed to allow for unobstructed fluid flow through hollow fiber bores. The hollow fibers are arranged into a structured cylindrical bundle and encased with an impermeable barrier except of a narrow gap adjacent to a tubesheet to allow for feed liquid entrance. This ensures directional fluid flow from the entrance end of the cartridge to the exit end of the cartridge. In some embodiments, the feed liquid is introduced on the bore side of hollow fibers and the extractant liquid is introduced on the shell side of hollow fibers.

The mesoporous asymmetric poly (aryl ether ketone) hollow fibers of this invention can be further coated with a polymer containing functional groups selective towards the solute to be transported across the membrane. The coating selective towards the solute can be formed on the exterior surface of the hollow fiber or on the lumen side of the hollow fiber and is preferably less than 5 microns thick, more preferably less than 1 micron in thickness.

Liquid-liquid extraction plays an important role in multistep chemical synthesis. It has the advantage of consuming low energy (compared to distillation) and is suitable for the purification of thermally sensitive compounds. In practice, multistage extraction or multiple washes is often required to achieve a high degree of separation, especially for systems with low partition coefficients or low selectivity. Multiple stages are typically cascaded into either cross-current or counter-current configurations. For a cross-current configuration, the extractant entering each stage is fresh, and the extract phase is not delivered to another stage but combined with the extract outlets from other stages. Therefore, the global flow direction of the two immiscible phases are defined as cross-flow. On the other hand, for the counter-current configuration, the two immiscible phases are globally moving in the opposite direction. In theory, for the same solvent usage, the countercurrent configuration yields the highest extraction efficiency. The counter-current flow configuration between the feed and the extractant liquids is advantageously utilized in LLE processes carried in the individual hollow fiber devices of this invention. To achieve a high degree of solute recovery, a multiple stage cascade process can be carried out in either cross-current or counter-current configuration. Hollow fibers with hydrophobic, hydrophilic or Janus surface characteristics are selected for optimal solute transfer in tailored membrane-assisted LLE extraction processes.

The present invention is described below by examples, which should not be construed as limiting the present invention.

EXAMPLES

Example 1

Figure 1B:
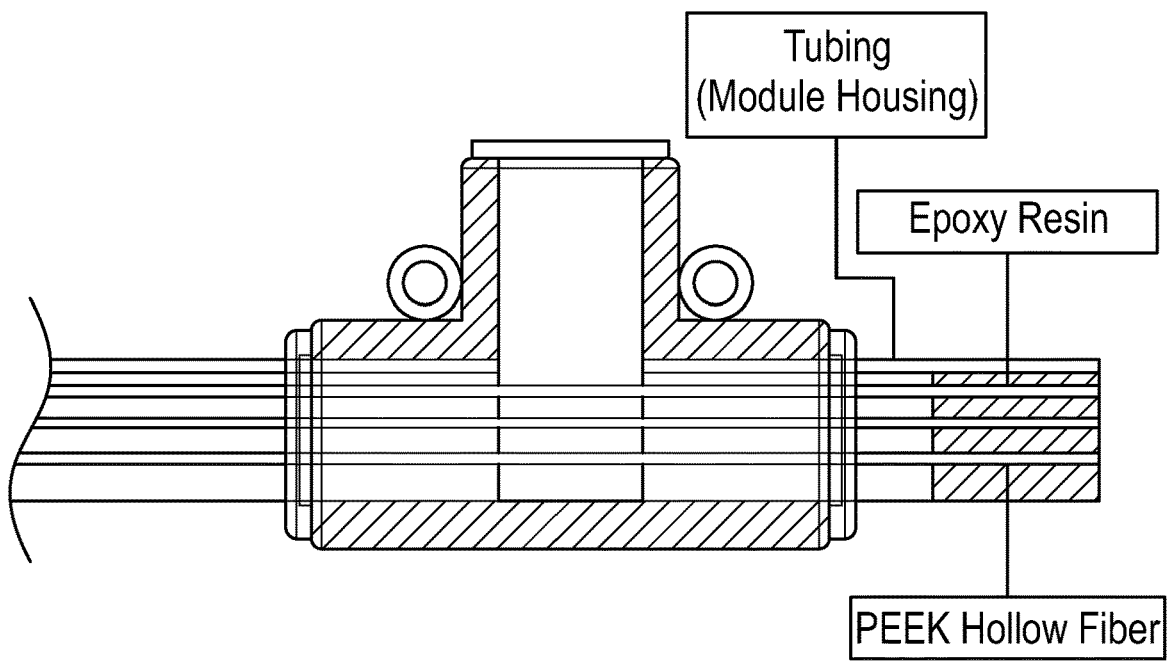
FIG. 1B shows in more detail an instrument fitting tee portion of the assembly of FIG. 1A.
Figure 1C:
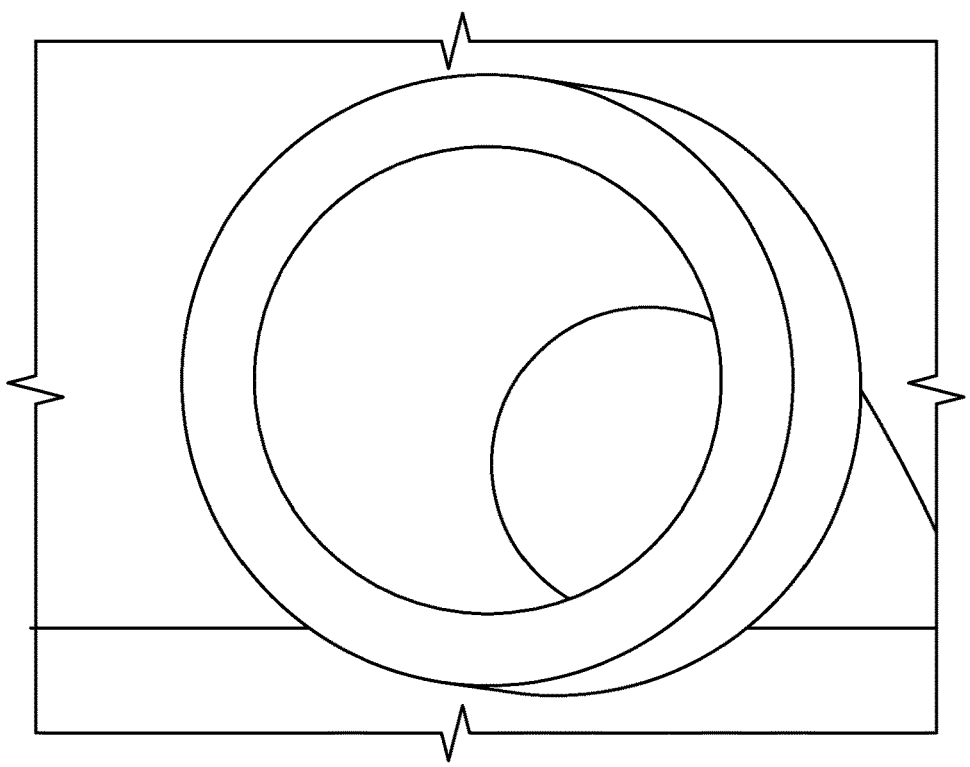
FIG. 1C shows in more detail a PEEK hollow fiber portion of the assembly of FIG. 1A.

This example describes the preparation of porous PEEK hollow fiber with hydrophobic surface characteristics. Poly (ether ether ketone) and polyetherimide, PEEK/PEI, blend (PEEK, Victrex 381G and PEI Ultem 1000; 35:65 by weight) was compounded in a twin extruder. A precursor non-porous hollow fiber was prepared by melt extrusion at circa 380° C. and quenched in water. The hollow fiber dimensions were 500 micron outside diameter and 320 micron inside diameter. Precursor hollow fibers were washed first with hexane, followed by immersing the hollow fiber into acetone maintained at 50° C. for 10 min to affect surface crystallization. Hollow fibers were then washed with water and heat-treated at 300° C. for 0.5 hour to affect the bulk crystallization of PEEK polymer in the blend. Hollow fibers were subjected to the RPR process by immersing fibers into the solution of NMP/monoethanolamine/water 80/10/10 by volume at 80° C. for 24 hours. The reservoir containing the solution was blanketed with nitrogen. The thus formed porous PEEK hollow fibers were washed extensively with distilled water, and fresh isopropyl alcohol, followed by distilled water. The hollow fibers were dried and used to construct a hollow fiber module. Gravimetric analysis indicated substantially complete removal of the polyetherimide. The porous PEEK hollow fibers were evaluated by ATR-FTIR and were essentially free of surface modification by the monoethanolamine via ketimine group formation. The surface area of the porous PEEK hollow fiber as measured by mercury intrusion porosimetry (MIP) was 70 m$^2$/g, with an average pore diameter of 70 nm. A 20 cm long hollow fiber module containing twelve hollow fibers was constructed and is shown schematically in FIGS. 1A-1C. The module was used for LLE processes. The hydrophobic hollow fiber membranes are to be preferred for LLE systems with distribution coefficient $m_i$>1.

Example 2

This example demonstrates the preparation of porous PEEK hollow fiber functionalized with hydroxyl groups by a selective reduction of surface ketone groups. Hollow fibers prepared as described in Example 1 were pre-dried in nitrogen while maintaining hollow fibers at 100° C. overnight. The pre-dried hollow fibers were treated with 1.0% w/v sodium borohydride solution in THF/PEG (1:1 ratio) for 4 hours while maintaining the solution at 50° C. The hollow fibers were then washed sequentially with dilute HCl solution (0.1N) and distilled water and then dried under nitrogen at 80° C. to a constant weight. The thus modified hollow fibers were found to be highly hydrophilic and easily wetted with water. ATR-FTIR spectra showed a significant reduction of >C=O group concentration (residual absorption of γ C=O at 1640 cm$^{-1}$ was attributed to crystalline regions not affected by modification); a high concentration of —OH groups was detected by ATR-FTIR (γ O—H peak at 3400 cm$^{-1}$) and attributed to the benzhydrol moiety of thus functionalized porous PEEK. The concentration of —OH groups was further determined by dissolving the functionalized PEEK hollow fiber in concentrated sulfuric acid and measuring the intensity of adsorption in UV-VIS spectra at 508 nm. The concentration of —OH groups was determined to be 0.8 mmol/g. A 20 cm long hollow fiber module was constructed and used for LLE processes. The module is shown schematically in FIGS. 1A-1C and contained twelve hollow fibers. The hydrophilic hollow fiber membranes are to be preferred for LLE systems with distribution coefficient $m_i$<1.

Example 3

This example demonstrates the preparation of PEEK hollow fiber with a layered hydrophilic and hydrophobic wall pore structure. Poly (ether ether ketone) and polyetherimide, PEEK/PEI, blend (PEEK, Victrex 381G and PEI Ultem 1000; 35:65 by weight) was compounded in a twin extruder. A precursor non-porous hollow fiber was prepared by melt extrusion at circa 380° C. and quenched in water. The hollow fiber dimensions were 500 micron outside diameter and 320 micron inside diameter. Precursor hollow fibers were washed first with hexane, followed by immersing the hollow fiber into acetone maintained at 50° C. for 10 min to affect surface crystallization. Hollow fibers were then heat-treated at 300° C. for 0.5 hour to affect the bulk crystallization of the PEEK polymer in the blend. The exterior surface of hollow fibers only was subjected to the RPR process (the hollow fiber bores were sealed to prevent contact with reagents). The RPR process was carried out by immersing fibers into the solution of NMP/monoethanolamine/water 80/10/10 by volume at 80° C. for 0.5 hours. The reservoir containing the solution was blanketed with nitrogen. The thus treated PEEK hollow fibers were washed extensively with fresh isopropyl alcohol, IPA. The hollow fibers were further treated with 1.0% w/v sodium borohydride solution in isopropyl alcohol for 8 hours while maintaining the solution at 50° C. The hollow fibers were then washed sequentially with dilute HCl solution (0.1N), distilled water, isopropyl alcohol and distilled water. The hollow fibers were subjected further to a second RPR process step to remove residual PEI from the fiber wall. Hollow fibers were subjected to the RPR process by immersing fibers into the solution of NMP/monoethanolamine/water 80/10/10 by volume at 80° C. for 8 hours. The reservoir containing the solution was blanketed with nitrogen. The thus formed porous PEEK hollow fibers were washed extensively with fresh isopropyl alcohol, IPA, followed by distilled water. Hollow fibers prepared as described above were pre-dried in nitrogen while maintaining hollow fibers at 100° C. overnight. The procedure produced hollow fibers of a layered structure with an exterior hydrophilic layer and an interior hydrophobic layer. The surface of thus modified hollow fibers was found to be highly hydrophilic and easily wetted with water. ATR-FTIR spectra of hollow fiber surface showed a significant reduction of >C=O group concentration); a high concentration of —OH groups formed was detected by ATR-FTIR ($\gamma$ 0-H peak at 3400 cm$^{-1}$) and was attributed to the benzhydrol moiety of thus functionalized porous PEEK. The bore side of hollow fibers remained hydrophobic. No change in the bore side surface chemistry was detected by the ATR-FTIR spectroscopy. The surface of the porous PEEK exhibited an average pore diameter of 12 nm as measured by atomic force microscopy. The bulk porosity was characterized by nitrogen adsorption BET. The membrane surface area was 80 m$^2$/g, with an average pore diameter of 32 nm. A 20 cm long hollow fiber module was constructed and used for LLE processes. The module contained 12 hollow fibers and is shown schematically in FIGS. 1A-1C. The LLE processes across hollow fiber membranes with the layered hydrophilic and hydrophobic porous wall structure are carried with the organic phase wetting the hydrophobic layer and the water-based solution wetting the hydrophilic wall layer.

Example 4

Hollow fiber modules prepared as described in Examples 1 and 3 were used to carry out LLE processes. The feed liquid was composed of toluene/n-heptane solution 50/50 by volume and the extractant liquid was NMP. The feed solution was introduced on the bore side of hollow fibers while the extractant liquid was flown counter-currently on the shell side of hollow fibers. The solute-toluene was transported across hollow fiber walls into the extractant. High feed flow conditions on the bore side were maintained thus the change in the toluene concentration in the feed fluid was small. The toluene was extracted into NMP extractant liquid and the concentration was measured. The toluene concentration in NMP was inversely proportional to the NMP flow rate and varied from 1% to 10%. Hollow fiber membranes showed good stability in solvent systems utilized.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A process of forming an asymmetric porous hollow fiber membrane comprising the steps of:
   (a) forming a blend of a poly (aryl ether ketone) polymer with a polyimide;
   (b) forming a hollow fiber shaped article from the blend by melt processing, wherein the article is substantially amorphous;
   (c) subjecting a surface of the article to a solvent treatment step that induces mobility of polymeric chains in the blend to cause crystallization in the article only to a predetermined depth in order to define a surface layer and an interior portion, the surface layer exhibiting a crystallization morphology while the interior portion remains substantially amorphous;
   (d) subjecting the article, subsequent to step (c), to a second crystallization step to complete crystallization such that both the surface layer and the interior portion exhibit crystallization morphologies, wherein the crystallization morphology exhibited by the surface layer is different as compared to the crystallization morphology exhibited by the interior portion despite both the surface layer and the interior portion being formed in step (b) from the same blend formed in step (a);
   (e) bringing the article into contact with a solution of primary amine or hydrazine to affect decomposition of the polyimide; and
   (f) removing products of polyimide decomposition from the article.

2. The process of claim 1 wherein functional groups are introduced on the surface of the article prior to step (e).

3. The process of claim 2 wherein the functional groups on the surface of the article are introduced via reaction with benzophenone segments of a polymeric backbone of the poly(aryl ether ketone) polymer.

4. The process of claim 3 wherein the functional groups on the surface of the article are reacted with functional organic molecules to form a separation layer covalently attached to the surface of the article via the functional groups.

5. The process of claim 2 wherein the functional groups are selected from: primary, secondary, tertiary or quaternary amine groups, a carboxyl group, a sulfonic acid group, a phosphate group, primary, secondary or tertiary hydroxyl groups, an ethylene oxide group and/or a sulfhydryl group.

6. The process of claim 1 wherein the crystallization in step (c) is carried out in an alcohol, a ketone, a chlorinated hydrocarbon, polyethylene glycol, an aromatic hydrocarbon or a mixture thereof.

7. The process of claim 6 wherein the ketone is an acetone, a methyl ethyl ketone, a 2-hexanone, an isophorone, a methyl isobutyl ketone, a cyclopentanone, an acetophenone, a valerophenone, a pentanone or a mixture thereof or a mixture with water.

8. The process of claim 1 wherein the surface layer is mesoporous.

9. The process of claim 8 wherein a thickness of the mesoporous surface layer is less than 1 micron.

10. The process of claim 1 wherein the poly (aryl ether ketone) comprises a poly (ether ketone), a poly (ether ether ketone), a poly (ether ketone ketone), a poly (ether ether ketone ketone) or a poly (ether ketone ether ketone ketone).

11. The process of claim 1 wherein the polyimide is a mixture of polyimides or a mixture of a polyimide with an additional pore-forming material.

12. The process of claim 1 wherein the polyimide is a poly (ether imide).

13. The process of claim 8 wherein the mesoporous surface layer exhibits an average pore diameter smaller by at least factor of two than an average pore diameter of the interior portion of the article.

14. The process of claim 13 wherein the average pore diameter of the surface layer is less than 70 nm.

15. The process of claim 8 wherein the mesoporous surface layer exhibits an average pore diameter falling within the range of 5 nm to 20 nm.

16. The process of claim 1 wherein the asymmetric porous hollow fiber membrane has a pore volume between 40 and 80%.

17. The process of claim 1 wherein the asymmetric porous hollow fiber membrane exhibits a degree of crystallinity of at least 20%.

18. The process of claim 1 wherein the crystallization in step (d) is carried out by a thermal treatment at a temperature between 210° C. and 310° C.

19. The process of claim 2 wherein the functional groups are formed by reduction of ketone groups in a benzophenone segment of the polymeric backbone to hydroxyl groups.

20. The process of claim 19 wherein the ketone group reduction is carried out utilizing sodium borohydride solution in an alcohol/water solvent mixture, or an alcohol/polyethylene glycol solvent mixture or a tetrahydrofuran/polyethylene glycol solvent mixture.

21. The process of claim 19 wherein the hydroxyl groups are further reacted with functional epoxide molecules.

22. A membrane reactor configured for transferring at least one molecule from a first fluid phase into a second fluid phase across an asymmetric porous hollow fiber membrane by contacting a first side of the asymmetric porous hollow fiber membrane with the first phase containing the at least one molecule dissolved in the first phase, contacting a second side of the asymmetric porous hollow fiber membrane with the second phase so that the first phase and the second phase come into contact through pores of the asymmetric porous hollow fiber membrane, and removing the first phase depleted of the at least one dissolved molecule from the first side of the asymmetric porous hollow fiber membrane while removing the second phase enriched with the at least one dissolved molecule from the second side of the asymmetric porous hollow fiber membrane, wherein the asymmetric porous hollow fiber membrane is formed by the process of claim 1.

23. The membrane reactor of claim 22 wherein the at least one molecule is a reactant transferred from the first phase into the second phase.

24. The membrane reactor of claim 22 wherein the at least one molecule is a reaction product removed from the first phase into the second phase.

25. The membrane reactor of claim 22 wherein no transfer of the first phase into the second phase takes place under conditions that a pressure differential existed between the phases.

26. The membrane reactor of claim 22 wherein the first phase is a gas and the second phase is a liquid.

* * * * *